(12) United States Patent
Smith et al.

(10) Patent No.: US 7,285,086 B2
(45) Date of Patent: Oct. 23, 2007

(54) MINIMALLY INVASIVE MEDICAL IMPLANT AND INSERTION DEVICE AND METHOD FOR USING THE SAME

(75) Inventors: Daniel J. Smith, Dayton, NJ (US); Michael Nordmeyer, Pittstown, NJ (US); Raimo Sump, Hamburg, DE (US); Susanne Landgrebe, Sulfeld, DE (US); Burkhard Peters, Wattenbeck, DE (US)

(73) Assignee: Ethicon, Inc., Somerville, NJ (US)

( * ) Notice: Subject to any disclaimer, the term of this patent is extended or adjusted under 35 U.S.C. 154(b) by 134 days.

(21) Appl. No.: 11/190,295

(22) Filed: Jul. 27, 2005

(65) Prior Publication Data

US 2006/0025783 A1 Feb. 2, 2006

Related U.S. Application Data

(60) Provisional application No. 60/700,857, filed on Jul. 20, 2005, provisional application No. 60/591,648, filed on Jul. 28, 2004.

(51) Int. Cl.
*A61F 2/00* (2006.01)
(52) U.S. Cl. .................................. 600/30; 606/148
(58) Field of Classification Search ............ 600/29–30, 600/37; 604/19, 27–28, 36, 48, 73, 500, 604/506, 511, 514–515, 517; 606/148, 151–156, 606/228, 232–233; 128/885, 887
See application file for complete search history.

(56) References Cited

U.S. PATENT DOCUMENTS

| 3,182,662 A | 5/1965 | Shirodkar |
| 3,311,110 A | 3/1967 | Singerman et al. |
| 3,472,232 A | 10/1969 | Earl |
| 3,608,095 A | 9/1971 | Barry |
| 3,763,860 A | 10/1973 | Clarke |
| 3,858,783 A | 1/1975 | Kapitanov et al. |

(Continued)

FOREIGN PATENT DOCUMENTS

DE 3223153 C 8/1983

(Continued)

OTHER PUBLICATIONS

International search report dated Nov. 25, 2005, for corresponding international application PCT/US2005/026637.

(Continued)

*Primary Examiner*—John P. Lacyk

(57) ABSTRACT

A medical device including an implant and inserter and a method for using the same. One embodiment includes an implant for implantation within a patient, and a first inserter for inserting the implant. The first inserter has a distal end region including a tissue penetrating distal tip, a proximal end region, a capture element located at the distal end region, and an implant holding element having a proximal end and a distal end. The distal end is removably received within the capture element, and the implant holding element further is movably coupled to the first inserter at a first location proximal of the capture element. The implant holding element extends from the first location at which it is movably coupled to the first inserter, and subsequently through the implant before being removably received within the capture element to thereby removably secure the implant to the insertion device.

26 Claims, 14 Drawing Sheets

U.S. PATENT DOCUMENTS

| | | | |
|---|---|---|---|
| 3,924,633 | A | 12/1975 | Cook et al. |
| 4,037,603 | A | 7/1977 | Wendorff |
| 4,128,100 | A | 12/1978 | Wendorff |
| 4,235,238 | A | 11/1980 | Ogiu et al. |
| 4,441,497 | A | 4/1984 | Paudler |
| 4,509,516 | A | 4/1985 | Richmond |
| 4,549,545 | A | 10/1985 | Levy |
| 4,946,467 | A | 8/1990 | Ohi et al. |
| 5,013,292 | A | 5/1991 | Lemay |
| 5,032,508 | A | 7/1991 | Naughton et al. |
| 5,080,667 | A | 1/1992 | Chen et al. |
| 5,112,344 | A | 5/1992 | Petros |
| 5,250,033 | A | 10/1993 | Evans et al. |
| 5,281,237 | A | 1/1994 | Gimpelson |
| 5,368,595 | A | 11/1994 | Lewis |
| 5,368,756 | A | 11/1994 | Vogel et al. |
| 5,383,904 | A | 1/1995 | Totakura et al. |
| 5,403,328 | A | 4/1995 | Shallman |
| 5,450,860 | A | 9/1995 | O'Connor |
| 5,507,796 | A | 4/1996 | Hasson |
| 5,582,188 | A | 12/1996 | Benderev |
| 5,611,515 | A | 3/1997 | Benderev et al. |
| 5,628,756 | A | 5/1997 | Barker, Jr. et al. |
| 5,645,568 | A | 7/1997 | Chervitz et al. |
| 5,647,836 | A | 7/1997 | Blake et al. |
| 5,665,096 | A * | 9/1997 | Yoon ............................ 606/139 |
| 5,741,299 | A | 4/1998 | Rudt |
| 5,816,258 | A | 10/1998 | Jervis |
| 5,836,315 | A | 11/1998 | Benderev et al. |
| 5,840,011 | A | 11/1998 | Landgrebe et al. |
| 5,855,549 | A | 1/1999 | Newman |
| 5,860,425 | A | 1/1999 | Benderev et al. |
| 5,899,909 | A | 5/1999 | Claren et al. |
| 5,899,999 | A | 5/1999 | DeBonet |
| 5,935,122 | A | 8/1999 | Fourkas et al. |
| 5,945,122 | A | 8/1999 | Abra et al. |
| 5,997,554 | A | 12/1999 | Thompson |
| 6,110,101 | A | 8/2000 | Tihon et al. |
| 6,117,067 | A | 9/2000 | Gil-Vernet |
| 6,221,005 | B1 | 4/2001 | Bruckner et al. |
| 6,306,079 | B1 | 10/2001 | Trabucco |
| 6,334,446 | B1 | 1/2002 | Beyar |
| 6,382,214 | B1 | 5/2002 | Raz et al. |
| 6,443,963 | B1 * | 9/2002 | Baldwin et al. ............ 606/148 |
| 6,475,139 | B1 | 11/2002 | Miller |
| 6,491,703 | B1 | 12/2002 | Ulmsten |
| 6,506,190 | B1 | 1/2003 | Walshe |
| 6,514,286 | B1 | 2/2003 | Leatherbury et al. |
| 6,605,097 | B1 | 8/2003 | Lehe et al. |
| 6,872,227 | B2 | 3/2005 | Sump et al. |
| 6,932,759 | B2 * | 8/2005 | Kammerer et al. ............ 600/30 |
| 2001/0018549 | A1 | 8/2001 | Scetbon |
| 2001/0049467 | A1 | 12/2001 | Lehe et al. |
| 2002/0028980 | A1 | 3/2002 | Thierfelder et al. |
| 2002/0058959 | A1 | 5/2002 | Gellman |
| 2002/0077526 | A1 | 6/2002 | Kammerer et al. |
| 2002/0099260 | A1 | 7/2002 | Suslian et al. |
| 2002/0120348 | A1 | 8/2002 | Melican et al. |
| 2002/0156488 | A1 | 10/2002 | Gellman et al. |
| 2002/0161382 | A1 | 10/2002 | Neisz et al. |
| 2002/0188169 | A1 | 12/2002 | Kammerer et al. |
| 2003/0023138 | A1 | 1/2003 | Luscombe |
| 2003/0062052 | A1 | 4/2003 | Carter et al. |
| 2003/0114866 | A1 | 6/2003 | Ulmsten et al. |
| 2003/0149440 | A1 | 8/2003 | Kammerer et al. |
| 2003/0176762 | A1 | 9/2003 | Kammerer |
| 2003/0191480 | A1 | 10/2003 | Ulmsten et al. |
| 2003/0225424 | A1 | 12/2003 | Benderev |
| 2004/0006353 | A1 | 1/2004 | Bosley et al. |
| 2004/0059356 | A1 | 3/2004 | Gingras |
| 2004/0087970 | A1 | 5/2004 | Chu et al. |
| 2004/0106847 | A1 | 6/2004 | Benderev |
| 2004/0111100 | A1 | 6/2004 | Benderev et al. |
| 2004/0122474 | A1 | 6/2004 | Gellman et al. |
| 2006/0058578 | A1 | 3/2006 | Browning |

FOREIGN PATENT DOCUMENTS

| | | |
|---|---|---|
| DE | 4220283 A1 | 12/1993 |
| DE | 10103179 A1 | 7/2001 |
| EP | 0668056 A1 | 8/1995 |
| EP | 0774240 A1 | 5/1997 |
| EP | 0941712 A1 | 9/1999 |
| EP | 1025811 A2 | 8/2000 |
| ES | 2226564 | 5/2003 |
| WO | WO96/06567 A1 | 3/1996 |
| WO | WO97/13465 | 4/1997 |
| WO | WO9831301 A1 | 7/1998 |
| WO | WO 00/27304 A1 | 5/2000 |
| WO | WO 00/74633 A2 | 12/2000 |
| WO | WO 01/06951 A1 | 2/2001 |
| WO | WO 02/28312 A | 4/2002 |
| WO | WO 0238079 A2 | 5/2002 |
| WO | WO 03/002027 A1 | 1/2003 |
| WO | WO 03/086205 A2 | 10/2003 |
| WO | WO 2004/004600 A1 | 1/2004 |
| WO | WO 2004/012626 A1 | 2/2004 |
| WO | WO 2004/060171 A1 | 7/2004 |
| WO | WO 2004/075936 A1 | 9/2004 |

OTHER PUBLICATIONS

Petros, P.E. Papa "Vault Prolapse II: Restoration of Dynamic Vaginal Supports by Infracoccygeal Sacropexy, an Axial Day-Case Vaginal Procedure", International Urogynecol Journal, Springer-Verlag London Ltd., 2001, vol. 12, pp. 296-303.

Petros, P.E. Papa "Vault Prolapse I: Dynamic Supports of the Vagina", International Urogynecol Journal, Springer-Verlag London Ltd.., 2001, vol. 12, pp. 292-295.

"TVT Tension-free Vaginal Tape, Minimally Invasive, Highly effective Treatment for Female Stress Urinary Incontinence", Gyncare, Ethicon, Inc., 1999, pp. 1-6.

"AMS Sparc Sling System", American Medical Systems, Inc., Minnetonka, MN, 2001, pp. 1-6.

Leanza, V. et al., New Technique For Correcting Both Incontinence And Cystocele: T.I.C.T. (Tension-free Incontinence Cystocele Treatment) Urogynaecologia International Journal, 2001, No. 3515, pp. 133-140.

Collinet, P. et al., "The Vaginal Patch For Vaginal Cure Of Cystocele", J. Cynecol. Obstet. Biol. Reprod. vol. 29, No. 2, (2000), pp. 197-201.

Cosson, M. et al., "Cystocele Repair By Vaginal Patch", Progres en Urologie, 2001, 11, pp. 340-346.

Giberti, C. "Transvaginal Sacrospinous Colpoplexy By Palpation—A New Minimally Invasive Procedure Using An Anchoring System", Urology, 57(4), 666-668 (2001), Elsevier Science Inc., Ospedale.

* cited by examiner

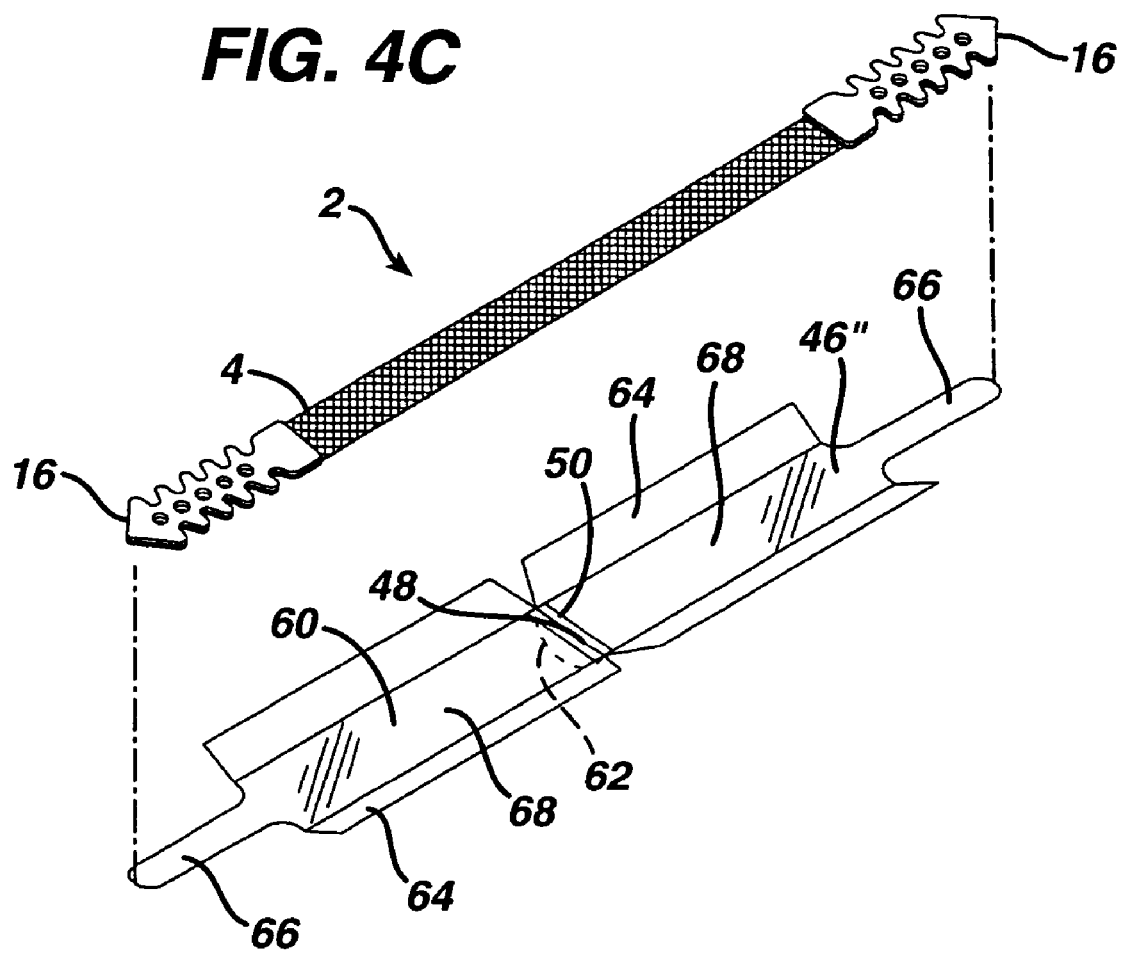

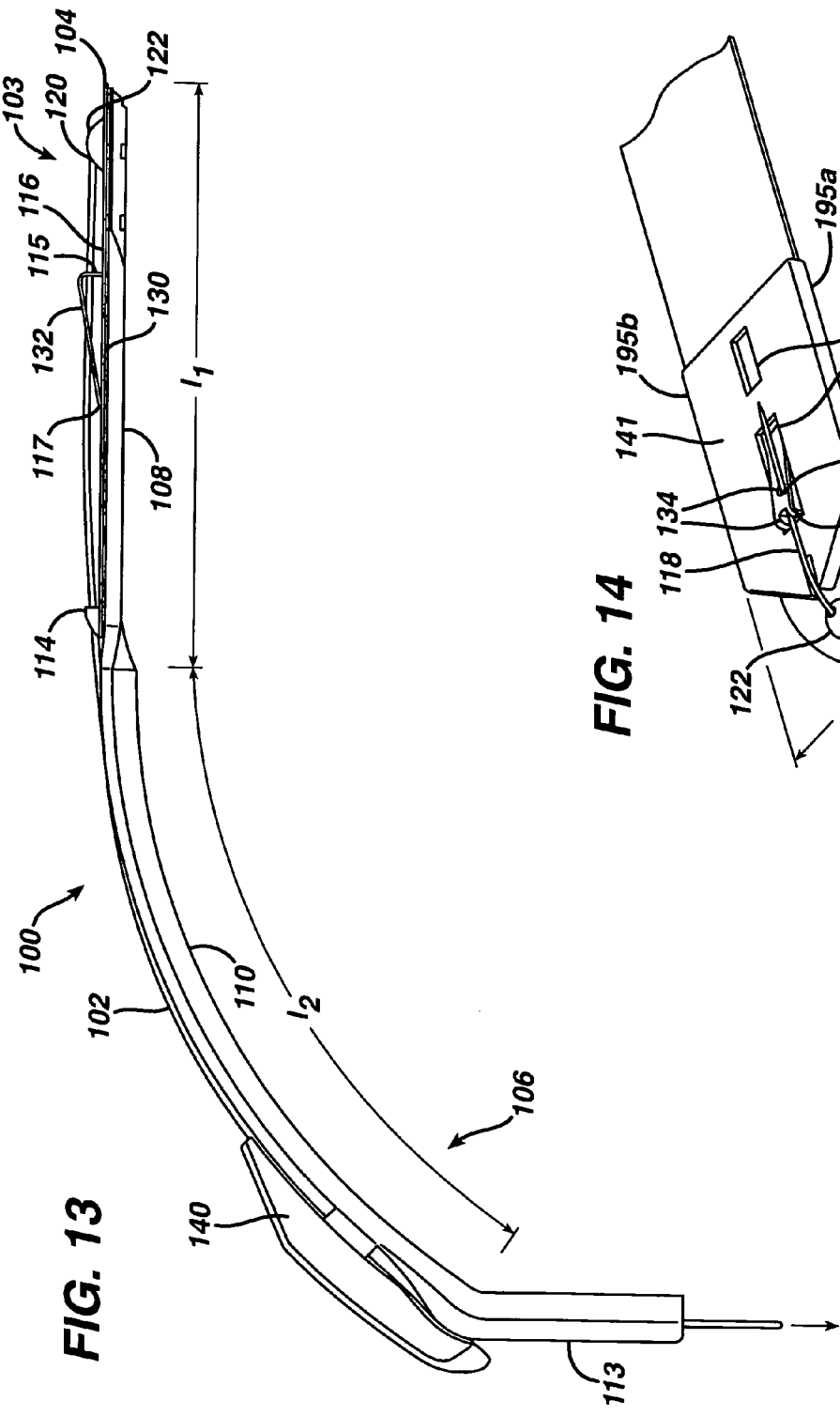

MINIMALLY INVASIVE MEDICAL IMPLANT AND INSERTION DEVICE AND METHOD FOR USING THE SAME

CROSS REFERENCE TO RELATED APPLICATIONS

The present application claims priority to U.S. Provisional Patent Application Serial Nos. 60/591,648, filed on Jul. 28, 2004, and 60/700,857, filed on Jul. 20, 2005.

BACKGROUND OF THE INVENTION

1. Field of the Invention

This invention relates generally to minimally invasive medical implants and procedures for their use and insertion device for implanting the same, having particular application for treating urinary incontinence.

2. Description of the Prior Art

Stress urinary incontinence (SUI) is a female medical condition commonly associated with weakening of the pelvic muscles and/or connective tissues that support the urethra in its proper position. As a result of this condition, involuntary urine leakage occurs from simple physical activity, such as running or jumping, and even coughing or sneezing, as the urethra is not properly supported and does not remain fully closed during such activity.

A widely accepted medical procedure to correct SUI is the insertion of a tension-free or trans-vaginal tape that is surgically implanted in the pelvic tissue and that extends under and provides support for the urethra when pressure is exerted thereon.

U.S. Pat. No. 5,899,909, the disclosure of which is incorporated herein by reference, describes in detail a typical procedure for treating SUI using a trans-vaginal tape. The tape is implanted by passing an elongated curved needle that is attached to one end of the tape through an incision in the vaginal wall, to one lateral side of the urethra, through the pelvic tissue behind the pubic bone, and exiting out through an incision made in the abdominal wall. The procedure is repeated for the other end of the mesh tape, this time on the other lateral side of the urethra, with the needle exiting through a second incision made in the abdominal wall of the patient. After the mesh tape is adjusted for proper support of the urethra, its free ends extending outside of the abdominal wall are trimmed. Over time, fibroblasts grow into the mesh tape to anchor the tape in the surrounding tissue. Thus, the tape is left as an implant in the body to form an artificial ligament supporting the urethra in order to restore urinary continence. In another known method for implanting a trans-vaginal tape, the tape is inserted in a somewhat similar manner, but is brought out through the obturator hole and exits the body through a small incision in the upper leg.

The use of trans-vaginal tape for treating SUI has a number of advantages. It does not need to be attached through bone anchors, sutures or any other element to secure the tape in place, and there is minimal scarring. The procedure takes about 30 to 50 minutes, and may be performed on an outpatient basis under local, regional or general anesthesia. One of the few disadvantages of known procedures for implanting sub-urethral tapes is that the use of needles to pass the tape through the body poses a risk for vessel, bladder and bowel perforation. Also they require two separate, minimal incisions made through the abdominal wall (for a retropubic approach) or the upper leg (for an obtuator approach) through which exit the curved needles and attached tape is passed. This, of course, increases the risk of post-operative pain and/or infection to at least a small degree.

Accordingly, what is needed is an improved sub-urethral tape, and device and method for implanting the same.

SUMMARY OF THE INVENTION

The present invention provides a medical implant inserter including an inserter device having a distal end region including a tissue penetrating distal tip, a proximal end region, a capture element extending outwardly therefrom, and a first pass through element extending outwardly therefrom and having at least one opening therethrough, with the pass through element being positioned at a location proximal of the capture element. The inserter device further includes an implant holding element having a proximal end and a distal end. The implant holding element is removably coupled at its distal end to the inserter device by being removably received within the capture element, and is movably coupled to the inserter device at a location proximal of the capture element. A portion of the implant holding element lies substantially adjacent to the inserter device, and a distal end portion extends to a position wherein it is spaced apart from the inserter device before being removably received within the capture element. The implant holding element passes through the at least one opening in the first pass through element to thereby at least partially maintain the position of the implant holding element relative to the inserter device.

A medical device is also provided including an implant for implantation within a patient, and a first inserter for inserting the implant. The first inserter has a distal end region including a tissue penetrating distal tip, a proximal end region, a capture element located at the distal end region, and an implant holding element having a proximal end and a distal end, the distal end of which is removably received within the capture element. The implant holding element further is movably coupled to the first inserter at a first location proximal of the capture element. The implant holding element extends from the first location at which it is movably coupled to the first inserter, and subsequently through the implant before being removably received within the capture element to thereby removably secure the implant to the insertion device.

Yet another medical device is provided having an implant for implantation within a patient having a first end, a second end, and top and bottom sides, and an inserter device for inserting the implant. The inserter device has a distal end region including a tissue penetrating distal tip, a proximal end region, a capture element positioned at the distal end region, and an implant holding element having a proximal end and a distal end that is removably received by the capture element when in a first position. The implant holding element is movably coupled to the inserter device at a location proximal of the capture element, and the implant holding element is movable to a second position wherein the second end is positioned proximal of and not received within the capture element. When the implant holding device is in the first position, at least a first end of the implant is positioned between the implant holding device and the inserter device to thereby secure the implant to the inserter device, and when the implant holding device is in the second position, the implant is not positioned between the implant holding device and the inserter, and is not secured thereto.

Finally, a method for implanting a suburethral implant is provided including the steps of providing an implant including an implantable, elongated tape having a multiplicity of openings formed therethrough, the tape having a first end region and a second end region longitudinally opposite the first end region, and first and second bio-compatible fixation elements attached to the first and second end regions respectively, and providing first and second insertion devices each including a first inserter having a distal end region including a tissue penetrating distal tip, a proximal end region, a capture element located at the distal end region, and an implant holding element having a proximal end and a distal end. The method further includes removably coupling the first and second fixation elements of the implant to the first and second inserters respectively by extending the respective implant holding element from a first location wherein it is movably coupled to the insertion device, through the fixation element and to a second location wherein its distal end is removably received within the capture element, inserting the first inserter and attached first fixation element through a vaginal incision and into a patient's tissue on a first side of the urethra, inserting the second inserter and attached second fixation element through the vaginal incision and into the patient's tissue on a second side of the urethra, adjusting the first inserter and attached fixation element and the second inserter and attached fixation element to thereby properly position the implant to provide support to the patient's urthra, uncoupling the first and second inserters from the first and second fixation elements substantially without further manipulation of the implant, and leaving the implant implanted within the body without further adjustment thereof.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 4C is a partially exploded isometric view of the implant shown in FIG. 4 with yet a further form of a protective sheath shown in an open state to receive the tape.

FIG. 13 is a side view of the insertion device of FIG. 12.

FIG. 14 is an enlarged view of the distal end region of the insertion device of FIG. 12 holding an implant.

DETAILED DESCRIPTION

Although the present invention is described in detail in relation to its use as a sub-urethral tape for treating stress urinary incontinence, it is to be understood that the invention is not so limited, as there are numerous other applications suitable for such an implant. For example, implants incorporating novel features described herein could be used for repairing pelvic floor defects such as, but not limited to, cystoceles and rectoceles, and for hernia repair or other prolapse conditions, or for supporting or otherwise restoring other types of tissue.

Figure 1:
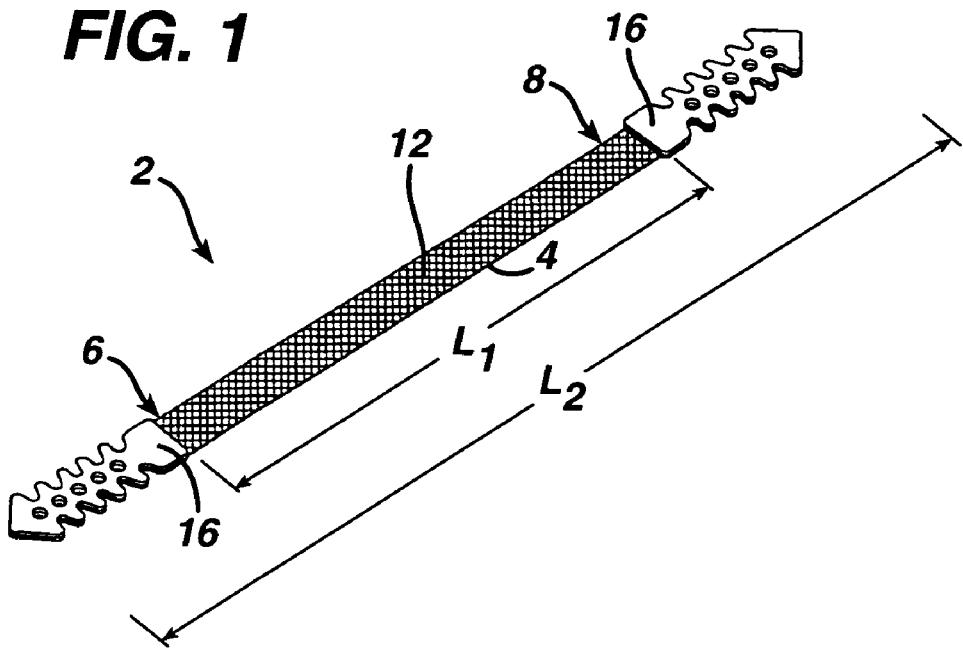
FIG. 1 is an isometric view of one example, of a medical implant in accordance with the present invention which is particularly suited for treatment of stress urinary incontinence.
Figure 2:
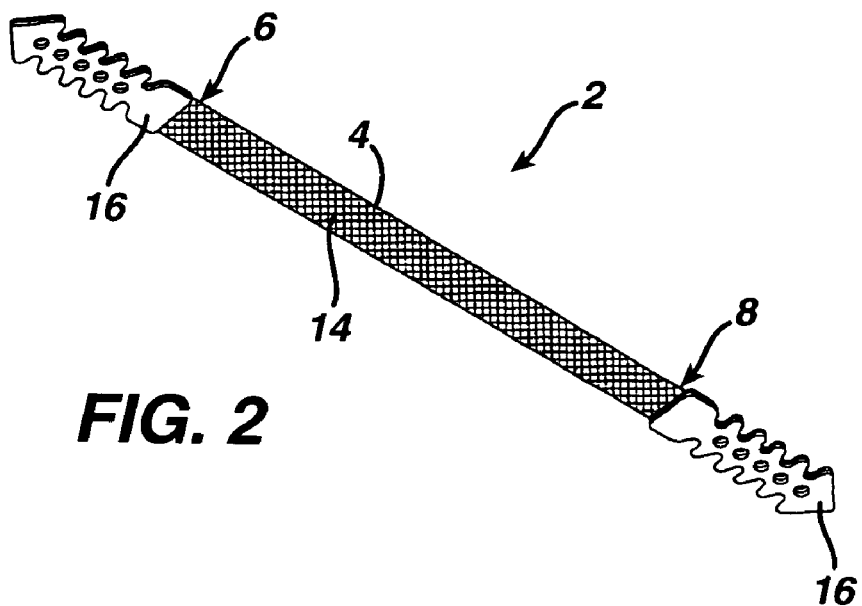
FIG. 2 is a bottom isometric view of the implant shown in FIG. 1.
Figure 3:
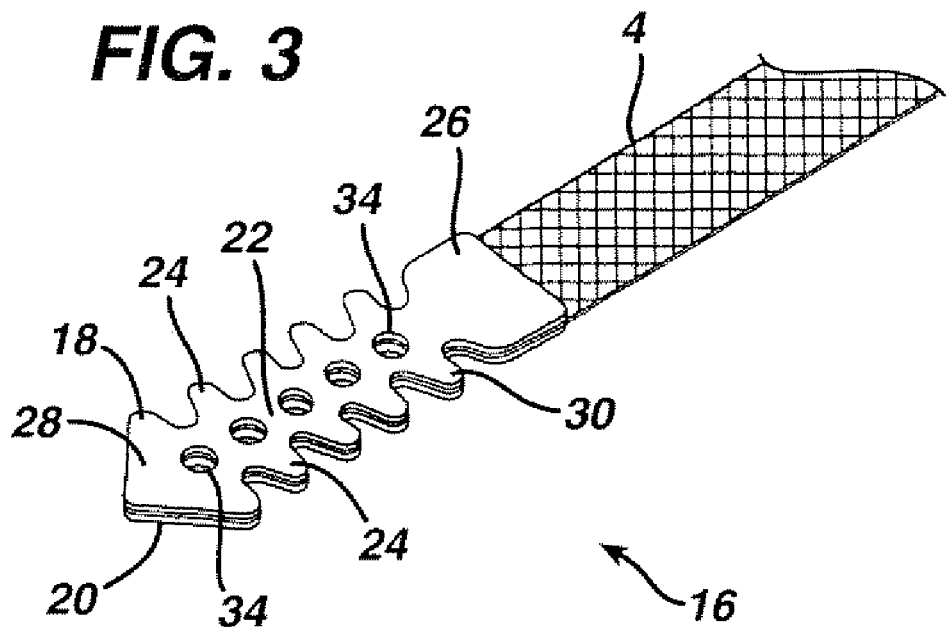
FIG. 3 is an enlarged isometric view of a portion of the implant formed in accordance with the present invention and shown in FIG. 1.

Turning initially to FIGS. 1-3 of the drawings, one embodiment of an implant 2 in the form of a sub-urethral tape particularly suited for the treatment of stress urinary incontinence (SUI) includes an implantable, elongated tape 4. The main tape portion 4 has a multiplicity of openings formed through the thickness thereof, and includes a first end 6 and a second end 8 longitudinally opposite the first end 6.

Preferably, the tape 4 is formed as a mesh or netting with openings formed through the thickness thereof of the order of about 1 millimeter to allow fibroblasts to grow into the tape for securing the tape in the surrounding tissue of the patient. A suitable material for the tape is PROLENE®, which is a knitted or woven polypropylene mesh having a thickness of approximately 0.7 millimeters, and which is manufactured by Ethicon, Inc., Somerville, N.J. This material is approved by the FDA in the United States for implantation into the human body.

The PROLENE® tape mentioned above is a non-absorbable mesh. However, it is envisioned to be within the scope of the invention to have the tape 4 formed of a knitted or woven material or netting that is bioabsorbable over time, or that can vary in pore size, fiber thickness, construction, size and/or properties.

The elongated tape 4 may be coated on one or more sides with a fibroblast stimulating substance, for example, an enamel matrix derivative.

Figure 5:
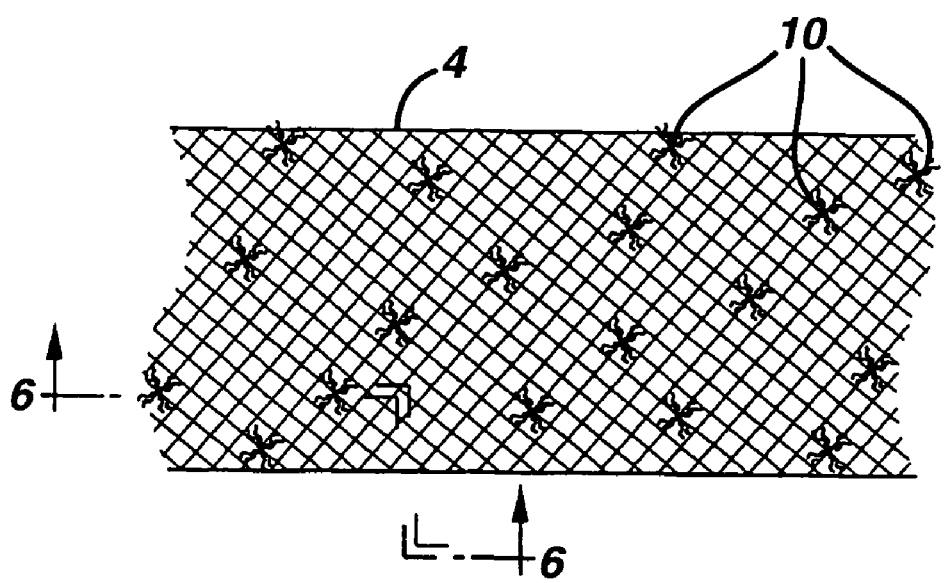
FIG. 5 is a top plan view of a portion of an implant formed in accordance with another embodiment of the present invention.
Figure 6:
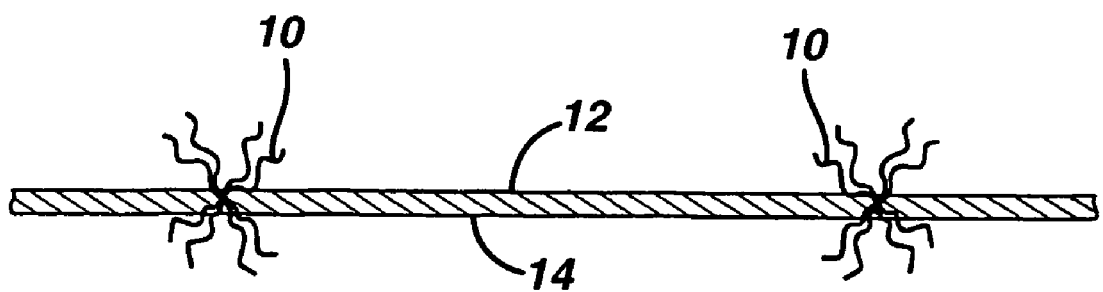
FIG. 6 is a cross-sectional view of the implant shown in FIG. 5, taken along line 6-6 of FIG. 5.

In a further embodiment shown in FIGS. 5 and 6, a plurality of spaced apart synthetic filament tangles 10 may be attached to the top side 12 and/or the opposite bottom side 14 of the tape 4 so as to extend outwardly from the surfaces of the top and bottom sides for stimulating scar tissue growth and attachment to the tape 4.

The visible mesh tape 4 will be suitably dimensioned in accordance with its application(s) as described. For example, one embodiment described in detail below that is particularly suitable for treatment of stress urinary incontinence in women has a width of approximately 10-12 millimeters, and has a length $L_1$ between about 15 millimeters and about 150 millimeters, preferably 40 millimeters. The total length of the implant $L_2$ including the fixation elements 16 can be from about 35 millimeters up to about 250 millimeters, and preferably about 80 mm millimeters. As will be explained in greater detail below, the length of the implant 2 may vary since the fixation elements 16 may be trimmed or cut transversely depending upon the insertion method and the needs of the physician during surgical implantation of the tape. Further, the length may vary according to the desired use and/or placement of the implant Returning again to FIGS. 1-3, the implant may further include a bio-compatible and preferably bio-absorbable polymer fixation element 16 attached to each of the first and second end regions 6, 8 of the visible main tape portion 4. In one embodiment, each bio-absorbable polymer fixation element 16 has tissue adherence properties for securing in vivo the implant to surrounding tissue of the patient in whom the implant is implanted without requiring any other means for physical attachment such as anchoring mechanisms or the like. By "tissue adherence property" what is meant is the ability of the implant to have relative immediate and positionable fixation (even if by temporary means) into sturdy tissue without the need for immediate tissue ingrowth. In yet another embodiment, the fixation elements simply have a stiffness greater than that of the main tape portion, which enables the fixation elements to be firmly held on to the insertion device, and when implanted within suitably sturdy tissue such as connective tissue, to be firmly held within the tissue. Other means for stiffening may also be used.

According to a preferred embodiment, the bio-absorbable fixation elements 16 are created by assembling material or components of a product sold under the name ETHISORB® Dura Patch, sold by Codman, a Johnson & Johnson company, which is mainly a VICRYL® polyglactin synthetic surgical composite material which is used for tissue reinforcement in surgery. VICRYL® is a material manufactured by Ethicon, Inc. of Somerville, N.J. ETHISORB® Dura Patch includes a fleece made from VICRYL® (polyglactin 910) and PDS (poly-p-dioxanone) undyed yarn which is sandwiched on one side with a piece of dyed poly-p-dioxanone film. The film and fleece are bonded together in a thermal process, which leaves the film intact as a sheet. The film is dyed violet with D&C Violet No. 2 (color index No. 60725). According to one embodiment, the ends of the PROLENE® tape can be sandwiched between two pieces of ETHISORB® Dura patch, with the components being thermally bonded together. According to a preferred embodiment, however, the VICRYL® and PDS components of ETHISORB® Dura patch are used to make the fleece portion, as well as the same dyed poly-p-dioxanone film. The separate components, the fleece pad and the dyed poly-p-dioxanone film sheet, are placed on one side of the PROLENE® tape and a second fleece pad and dyed poly-p-dioxanone film sheet are placed on other side. The 5-piece assembly is then placed into a thermal process to bond the components together. The thermal process is controlled to maintain the temperature such that it only will melt the PDS yarn and dyed poly-p-dioxanone film. Use of the separate components provides a non-pressed fleece that facilitates subsequent bonding of the two film sheets through the mesh, since the two fluffy fleece layers integrate into the weave of the PROLENE® mesh during pressing. After the thermal pressing process, the dyed poly-p-dioxanone film sheets no longer exist, as they are melted forming a plethora of bond points between the mesh and fleece layers.

The fleece component described above is made from absorbable materials, but could conceivable be made from non-absorbable material or a combination thereof. The process of making the fleece starts similar to other textiles where relatively straight yarn is taken in a preferred ratio, with the ratio of VICRYL® to PDS in the preferred embodiment being approximately 8:1. The single yarn strands are spun together using common textile techniques, and the new strand is woven into a sock like structure that is approximately 1-2 inches in diameter and of a continuous length. The sock or tube like structure is woven so that the lead thread can be pulled to unravel the tube, which kinks the otherwise relatively straight 8:1 strand.

The sock or tube is fed into a loom, and a loose scarf-like material sheet is woven approximately 8 inches wide. Because the kinked 8:1 strand was used, the resulting scarf structure is fluffy. The scarf is then cut into lengths of approximately 12-18 inches. The cut length is then place on a non heated plate, and a heated plate then dropped over the non-heated plate trapping the scarf between a defined gap. As the temperature of the scarf increases to a predetermined temperature that is below the PDS yarns melting point, small melting points are generated that hold the shape of the new fluffy fleece structure. As the individual PDS yarn strands shrink and melt slightly they pull the VICRYL® yarn strands with it. Further, as the original scarf shrinks, it gets both thicker and smaller as the open weave of the scarf closes up. The resulting new material is an exemplary "fleece like material" as referenced above.

Although one preferred embodiment is described above, it is recognized that improvements can be made that are intended to be within the scope of the present invention. For instance, one may alter the compositional ratio of absorbable polymers making up the material. That is, use more of the poly(L(-)-lactide-co-glycolide) component and less of the poly(p-dioxanone) component, or vice versa. It is also recognized that in the case of the lactide/glycolide copolymer, one might alter the relative amounts of the co-monomers. Thus one might slightly increase the lactide level in the copolymer to reduce crystallinity and increase the rate at which the component is absorbed. It is also recognized that the geometrical nature of the fibrous components of the fleece can be altered to provide enhanced gripping of the tissue surfaces. One may provide a more non-circular cross-section of the fibrous components, such as a cross-section that is flatter. A star-shaped cross-section might also be utilized to enhance gripping.

Further, other absorbable polymers might be utilized to advantage in practicing the present invention. Of particular utility are the absorbable or bioabsorbable polymers prepared from lactone monomers selected from the group consisting of p-dioxanone, glycolide, L(-)-lactide, D(+)-lactide, meso-lactide, ε-caprolactone and trimethylene carbonate or combinations thereof. In those surgical cases in which tissue repair is compromised, such as in diabetic or elderly patients, the absorption profile of the fixation elements might be adjusted accordingly. Thus, one might make use of a high-lactide (co)polymer, such as 95/5 poly(L(–)-lactide-co-glycolide) to advantage.

Besides the absorbable polymers prepared from lactone monomers described above, one might utilize oxidized regenerated cellulose, also known as ORC. This material, especially in a non-neutralized state, is known to adhere to bodily tissue. The extent of oxidation and acidity could be adjusted to enhance the adherence and also provide antibacterial activity.

In a further aspect of the invention, the absorbable polymers may be combined with antimicrobial agents to provide an added benefit. It is recognized that other active ingredients might be added to provide enhanced characteristics, such as pain reduction agents, etc. The agents may be added to the polymer prior to formation of the final material, added to the final material once fabricated, or added to the fixation elements once fabricated.

It would not be unreasonable to assume that there are certain surgical situations in which a non-absorbable permanent fixation elements would be preferred. In this case the fixation elements could be fabricated from a variety of materials, including but not limited to non-absorbable polymers, metals, or ceramics. Non-absorbable polymers include the polyolefins, such as polyethylene or polypropylene; polyurethanes; polyesters, such as polyethylene terephthalate or polybutylene terephthalate; and polyamides, also known as nylons, such as nylon-6, nylon-66, or nylon-12.

As shown in the embodiment of FIG. 3 and as described above, each fixation element 16 may include a first top portion 18 and a second bottom portion 20. The first portion 18 is attached to the top side of the tape and the second portion 20 is attached to the bottom side of the tape. The tape may extend along only a portion of the length of the fixation element, or in alternate embodiments may extend fully along the length or simply secured to the extreme ends of the tape. The fixation element portions 18, 20 may alternatively be attached to the tape 4 by other well-known methods, such as by using bio-compatible adhesives or the like.

The polymer fixation elements 16 of the embodiment of FIGS. 1-3 include a central body portion 22 and a plurality of longitudinally spaced apart finger portions 24 extending outward laterally in opposite directions from the central body portion 22. Preferably, each finger portion 24 is generally triangular in shape, with the polymer fixation element 16 taking on a generally arrow configuration, with a broad base 26 at one end and a triangular or arrowhead-shaped tip portion 28 at the other end. The plurality of triangular-shaped finger portions 24 extend laterally outwardly between the base 26 and triangular tip portion 28.

The triangular-shaped finger portions 24 may be spaced apart longitudinally from adjacent finger portions by about 3-5 millimeters, and the fingers on either side of the center portion may be shifted to further enhance adjustability. The width of each polymer fixation element 16 measured between the most lateral extent of transversely disposed finger portions 24 is preferably about 11 millimeters, which is the preferred width of the tape 4 and the implant 2 overall. In an alternate embodiment, the fingers may be very closely spaced, on the order of 0.02 to 1.0 millimeters, and may have any configuration other than triangular, so as not to resemble visible fingers. The implant may further include interruptions in the pitch between the "fingers." For example, in one preferred embodiment, the "fingers" are spaced apart longitudinally by approximately 0.05 mm, with every other one removed. Alternatively, an irregular cut surface that has no defined spacing longitudinally along it can be used on one or both sides.

The finger portions 24 can be sharp, but preferably are formed with a radius of about 0.1 and 2 millimeter at their most laterally outwardly extending part 30, and are formed with a radius of about 0.1 and 2 millimeter at their most inwardly extending part 30, i.e., the area in between adjacent laterally outwardly extending portions 30 thereof, and the triangular tip 28 of each fixation element 16 has a transverse width of about 11 millimeters and a longitudinal length that can vary from 3-10 millimeters. Furthermore, the fixation elements 16 may be trimmed or cut across their transverse width if the physician needs to shorten the overall length of the implant 2.

With this particular shape, the polymer fixation elements 16 are envisioned to adhere to and/or engage the surrounding tissue, minimizing backward slippage or forward sliding after the implant 2 is surgically implanted in the patient. It is preferred that each fixation element 16 have a stiffness that is greater than the stiffness of the mesh tape portion 4 in order to provide some rigidity and maintain its overall shape. This prevents or minimizes slippage with respect to the surrounding tissue to which they adhere and maintains the overall integrity of the fixation elements during surgical implantation. Stiffness of the whole fixation area can be changed through choice of manufacturing process.

Figure 10:
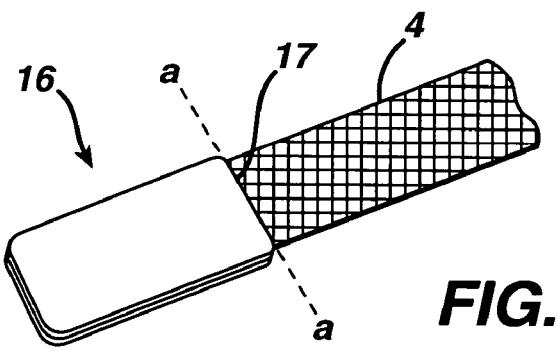
FIG. 10 illustrates one end of another embodiment of an implant according to the present invention.
Figure 10A:
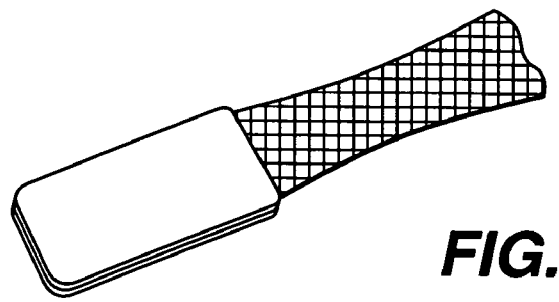
FIG. 10a illustrates the shape of the implant of FIG. 10 when implanted and under tension.

Although the embodiment of FIGS. 1-3 incorporates the finger portions described above, the fixation areas may also simply have a rectangular configuration, as shown in FIG. 10, so long as the fixation areas are comprised of a material having a suitable stiffness and/or tissue adhesive properties to secure the tape in place, such as the material described above. In the embodiment of FIG. 10, a lower edge 17 of the fixation area 16 has a cross-sectional area (along line a-a) that is slightly larger than that of the mesh to which it attaches. This difference in cross-sectional area may also be increased during implantation since typically the tension on the mesh causes the mesh to assume a slightly reduced width as shown in FIG. 10a.

Figure 9:
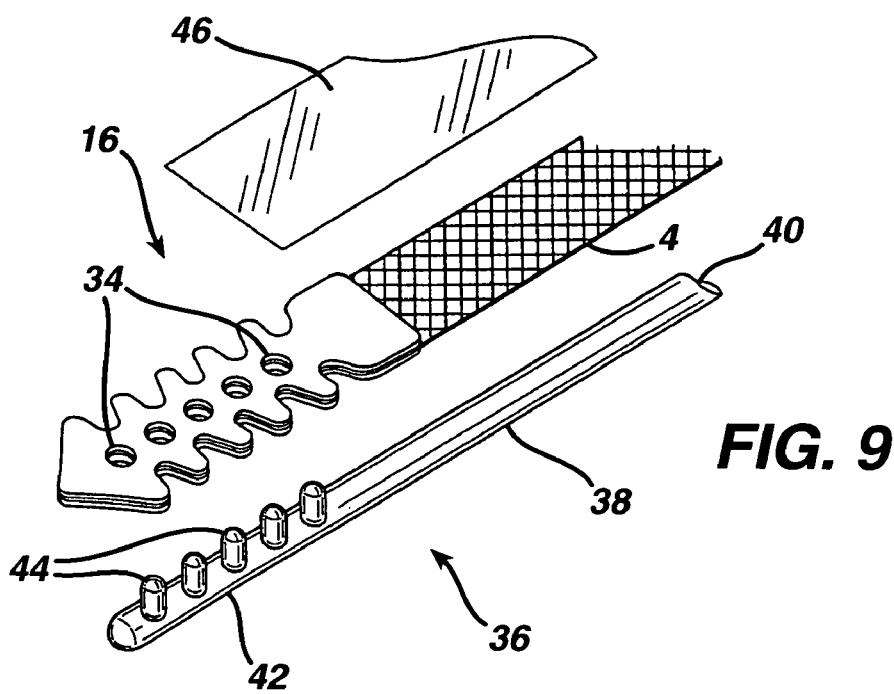
FIG. 9 is a partial isometric and exploded view of one form of an insertion tool, shown overlying one end of an implant, both of which are formed in accordance with the present invention, for surgically implanting the implant in the body of a patient.

As shown in FIG. 9 in particular, each fixation element 16 may further include one or more holes 34, openings, slits or the like formed through the thickness thereof and longitudinally spaced apart from each other. These holes 34 may cooperate with one embodiment of an insertion tool 36 for properly positioning the free ends of the implant 2 in the pelvic or obturator tissue of the patient. Such an insertion tool 36 may include an elongated rod 38 which may be bendable to a desired curvature by the physician and which retains its configured shape during the surgical procedure. The rod 38 includes a proximate end 40 for grasping by the physician, and a distal end 42 opposite the proximate end 40 for insertion through an incision made in the top vaginal wall of a patient. The distal end portion 42 includes one or more prongs 44 extending radially outwardly from the rod 38 and spaced apart from one another. Each prong 44 has a diameter that is equal to or slightly less than the diameter of the holes 34 formed in the fixation elements 16, and adjacent prongs 44 are separated from one another a distance equal to the spacing between adjacent holes 34 formed in the fixation elements. Accordingly, the prongs 44 of the insertion tool 36 are receivable by the holes 34 formed in the fixation elements 16 so that each free end of the implant 2 may be selectively secured to the distal end 42 of the insertion tool for proper placement within the pelvic tissue of the patient. Once properly positioned, the implant 2 may be separated from the insertion tool 36 by the physician manipulating the proximate end in order to maneuver the distal end 42 of the insertion tool slightly away from the implant 2 so that the prongs 44 are released from their respective holes 34 in the fixation elements. Various other methods of insertion will also be apparent to those skilled in the art, such as any variation of a forcep used to position the fixation areas, or other insertion tools having suitable means by which to grasp and/or position the fixation areas of an implant. Another preferred embodiment of an insertion device will be described in detail below.

A second reason for having such holes 34 formed through the thickness of the fixation elements 16 is that they facilitate the in-growth of tissue through the fixation elements to further adhere them to the surrounding tissue.

Figure 4:
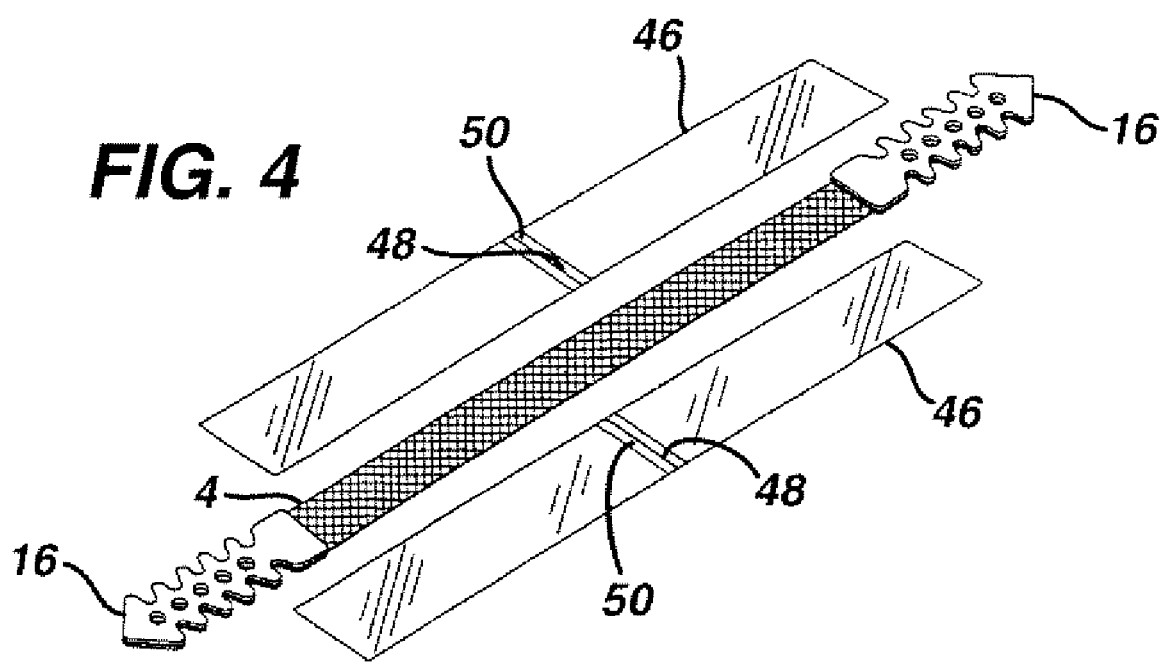
FIG. 4 is a partially exploded isometric view of the implant shown in FIG. 1 and shown with one example of a protective sheath.

As shown in FIG. 4 of the drawings, according to one embodiment, the implant 2, and in particular the tape 4 is covered on its top and bottom sides with a removable plastic sheath 46. Each sheath 46 may include a cut or perforation 48 extending at least partially across its width at its midpoint that overlies the midpoint of the implant 2 to facilitate its removal from the top and bottom sides 12, 14 of the tape 4. It may further include a line or other marking 50 running transversely across the middle of the sheath 46, with such line or other marking 50 being positioned at the midpoint of the implant 2 so as to indicate to the physician where the midpoint of the tape resides during the surgical implantation procedure. Forceps may be used to remove the sheath 46 from the top and bottom sides 12, 14 of the tape 4 during the implantation procedure. The sheaths 46 may prevent the tape 4 from catching on the surrounding tissue during insertion and positioning of the implant 2 within the patient's body. Each sheath 46 preferably extends slightly beyond the width of the tape 4 to ensure that the top and bottom sides 12, 14 and the lateral edges of the tape 4 will not catch on the surrounding tissue during the surgical procedure. A sheath may also allow protection against contamination or damage.

Figure 4A:
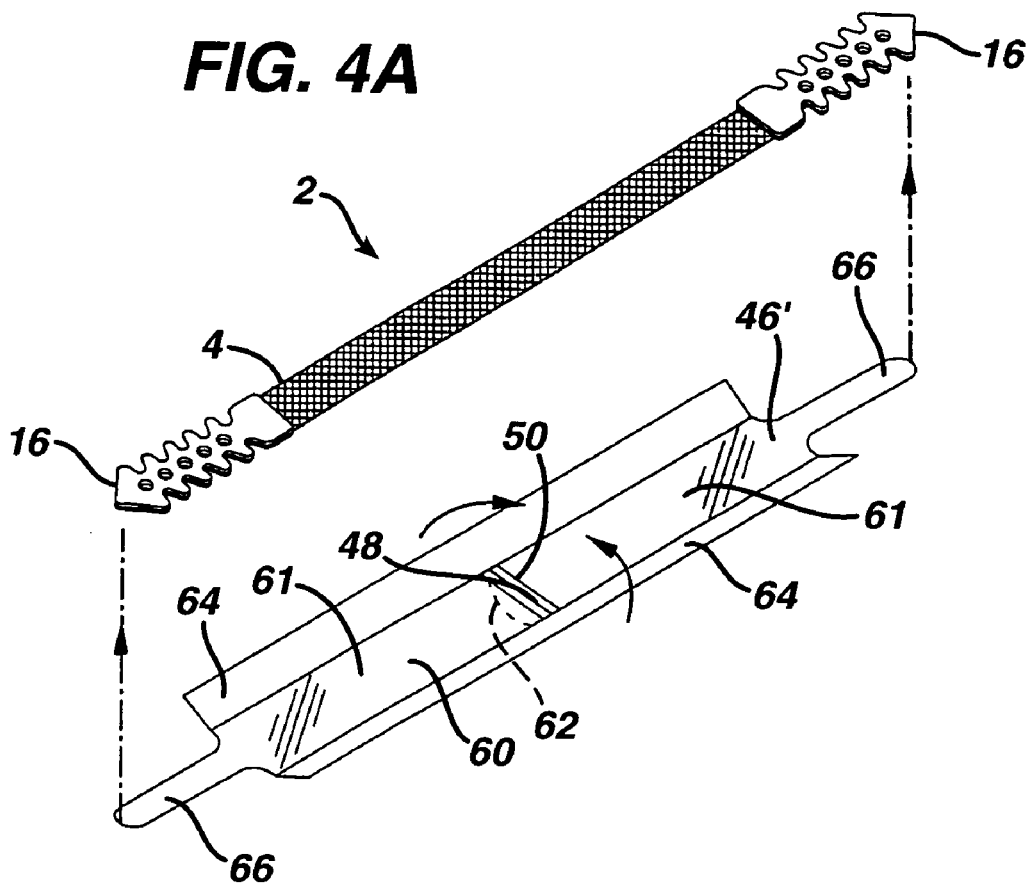
FIG. 4A is a partially exploded isometric view of the implant shown in FIG. 4 with another form of a protective sheath shown in an open state to receive the tape.
Figure 4B:
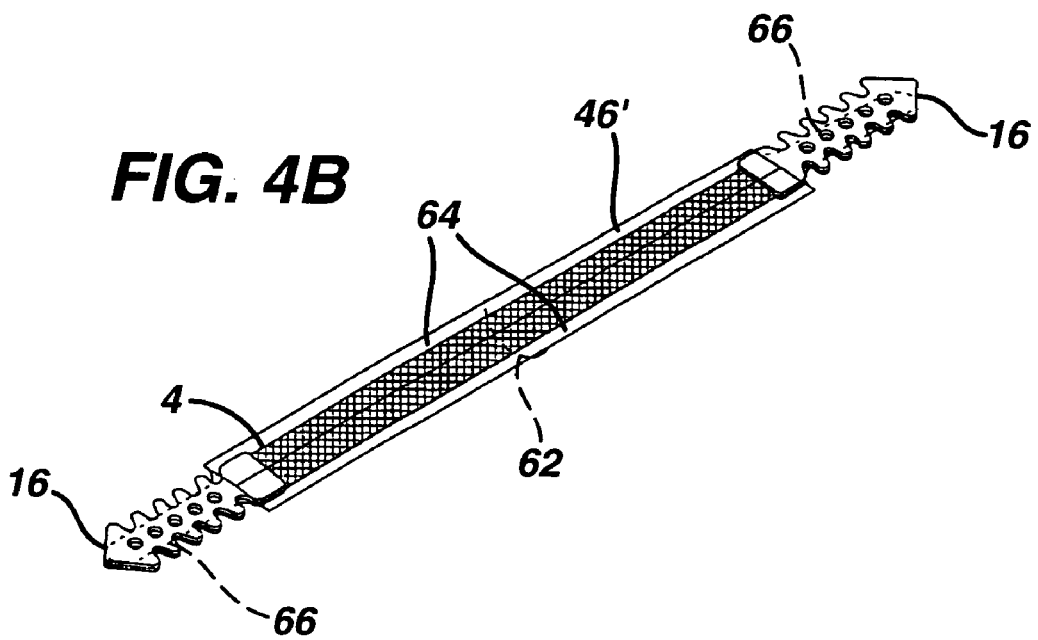
FIG. 4B is an isometric view of the implant and protective sheath shown in FIG. 4, the protective sheath being shown folded to at least partially envelop the tape.

Other forms of protective sheaths are illustrated by FIGS. 4A-4C. More specifically, FIGS. 4A-4C illustrate protective sheaths for the implant that are formed as wrappers that may be folded over the implant to at least partially envelop the tape during implantation.

Turning initially to FIGS. 4A and 4B, the protective sheath 46' includes a back piece 60, preferably formed of two segments 61 positioned end-to-end. In relation to the tape, the two segments 61 meet in preferably the middle of the tape and extend perpendicularly outwardly from the outer surface of the back piece to define together a tab 62. Each segment 61 of the back piece 60 forming the tab 62 may be grasped by the physician using forceps to remove the protective sheath 46' from the implant 2 after it has been properly positioned and implanted in the patient.

The protective sheath 46' further includes foldable lateral pieces 64 attached to and extending from opposite sides of the back piece 60 at least partially along the longitudinal length of the back piece. As can be seen in FIG. 4B, the implant 2 and sheath 46' are assembled such that the bottom side of the implant rests on the inner surface of the back piece 62, and the lateral pieces 64 of the sheath are folded over the top side of the implant. The lateral pieces 64 of the sheath 46' may be dimensioned to meet each other at their free edges along the longitudinal centerline of the implant, or may be dimensioned so that one lateral piece extends partially overlapping the other lateral piece.

Preferably, as shown in FIGS. 4A and 4B, the protective sheath 46' may further include axial end pieces 66 attached to and extending from opposite axial sides of the back piece 60. Each axial end piece 66 is preferably dimensioned to have a width and length that conform to the width and length of the central body portion 22 of each fixation element 16 so that they cover only one side of the central body portion 22, leaving the other side of the central body portion 22, and both sides of the finger portions 24, exposed. In this way, during implantation and with the protective sheath 46' affixed to the implant 2, the exposed portions of the fixation elements 16 will contact and be able to adhere to the surrounding tissue of the patient.

FIG. 4C illustrates another form of a protective sheath 46" for use with the implant of the present invention. This sheath 46" is the same as that shown in FIGS. 4A and 4B, except that it is formed in two longitudinally disposed, individually foldable halves, i.e., the back piece 60 and opposite lateral pieces 64 are each formed by two separable segments 68 positioned longitudinally to each other in an end-to-end fashion. Each half portion segment 68 of the sheath 46" may be removed separately in the same manner as described previously, that is, by the physician grasping portions of the sheath back piece forming the tab 62 with forceps, so that one half segment 68 of the sheath 46" may be removed, if desired, during partial implantation of the implant, or both half segments 68 may be removed after both ends of the implant 2 have been properly positioned and implanted in the patient.

Additionally, the tape 4 may have its top side 12 formed with one marking, such as a first color, and its bottom side 14 formed with another marking, such as a second color that is different from the first marking or color. This will allow the physician to know whether the tape 4 is or has twisted during the surgical implantation procedure. In other words, one of the top and bottom sides 12, 14 of the implant 2 should be facing toward the urethra as it is looped partially thereabout, and the other of the top and bottom sides 12, 14, having a different color or other marking which is visible to the physician, should be facing away from the urethra during its surgical implantation in the patient. Of course, it is envisioned that the sheath 46, 46', 46", instead of the implant 2, may be similarly colored or include distinguishing markings.

In addition to the mentioned markings on the fixation ends, the mesh or sheath may be marked to describe the center of the mesh loop or a zone may be marked to help the physician symmetrically locate the mesh loop relatively to the urethra during implantation.

Figure 7:
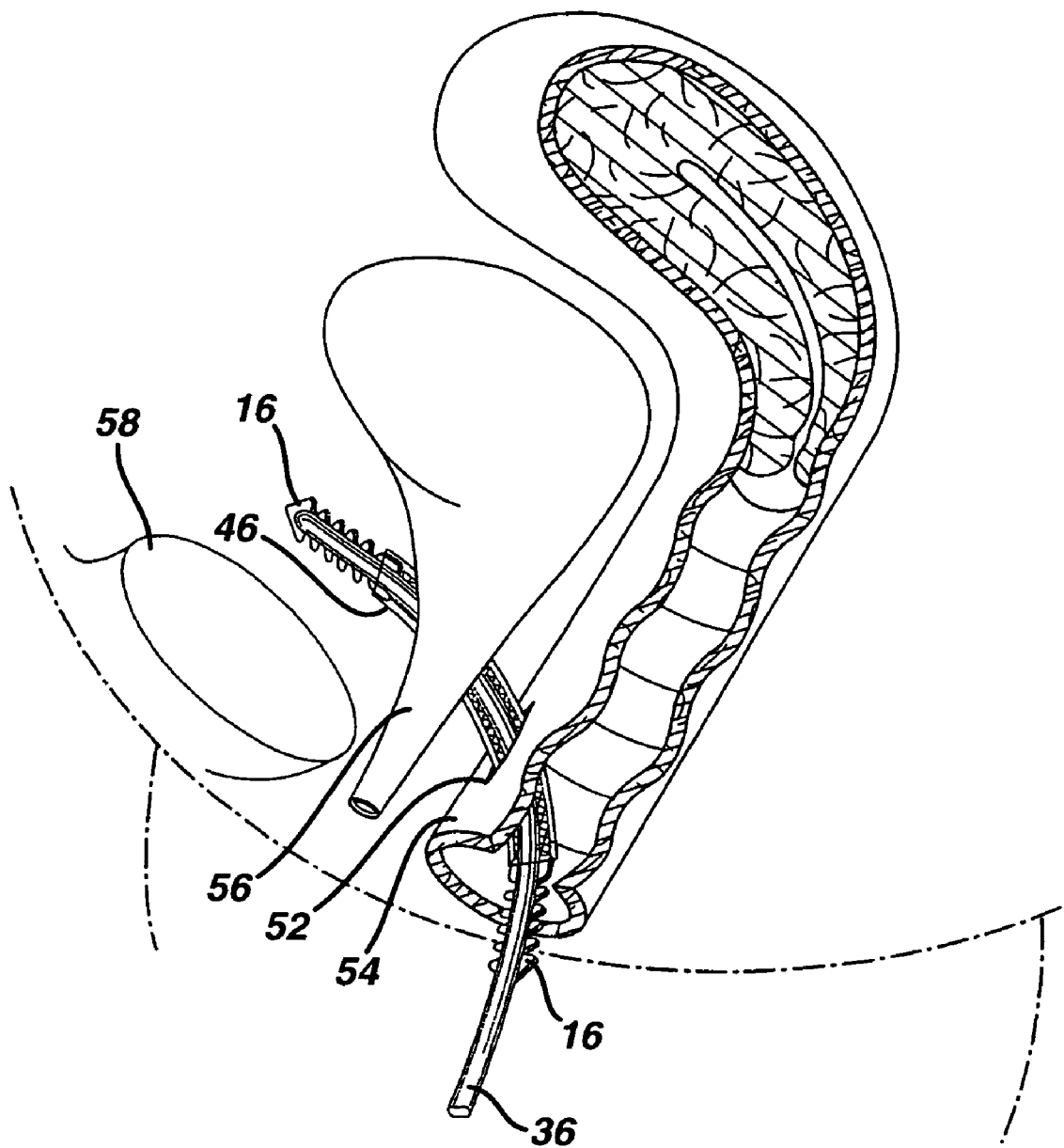
FIG. 7 is a diagrammatic illustration of an implant of the present invention being surgically implanted in the body of a patient prior to sheath removal.
Figure 8:
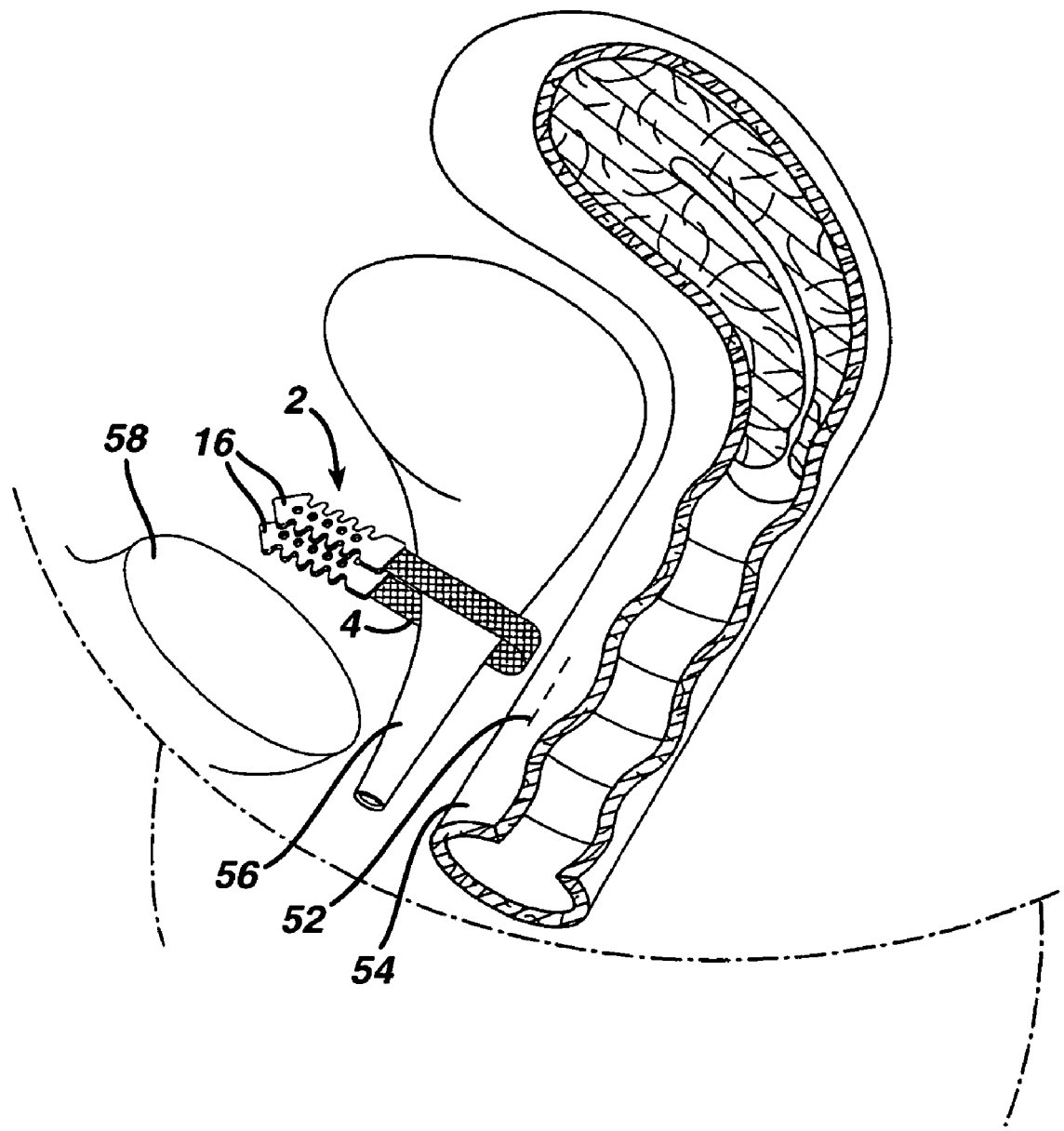
FIG. 8 is one diagrammatic illustration of an implant of the present invention shown surgically implanted in the body of a patient after proper placement and sheath removal.

FIGS. 7 and 8 illustrate one procedure for surgically implanting an implant 2 of the present invention in a patient to treat stress urinary incontinence (SUI). First, a small incision 52 is made in the top vaginal wall 54. The physician attaches the distal end 42 of the insertion tool 36 to one fixation element 16 of the implant 2 by inserting the prongs 44 into their corresponding holes 34 formed through the fixation element. The physician may bend the insertion tool to whatever curvature he feels is necessary to aid in the implantation procedure.

By manipulating the proximate end 40 of the insertion tool 36, the physician directs the distal end 42 of the tool with one end of the implant 2 attached thereto through the surgical incision 52 and into the soft tissue on one lateral side of the urethra 56 and behind the pubic bone 58. The transverse marking(s) 50 on the sheath 46, 46', 46" will indicate to the physician the midpoint or mid-zone of the implant 2 so that the physician can judge the extent of tissue penetration and whether further insertion is required. Due to its inherent tendency to adhere to the surrounding tissue, the fixation element 16 secures the free end of the implant 2 to the surrounding tissue it contacts. The physician now manipulates the insertion tool 36 such that it frees itself of the fixation element 16 and is removed, leaving the first half of the implant 2 implanted in the patient.

With the described insertion concept, and after insertion of the first fixation element, the physician may recognize that the implant is too long by comparing the middle marking or mid-zone of the implant with the position of the urethra. If necessary, the second fixation element 16 of the described implant may be trimmed to compensate for the difference in length. Once trimmed to length, the physician then attaches the distal end 42 of the insertion tool to the fixation element 16 at the other end of the implant 2, and directs the tool again through the vaginal wall incision 52 and so as to pass through the soft tissue on the other lateral side of the urethra 56 and behind the pubic bone 58. The physician then separates the insertion tool 36 from the fixation element 16 at this second end of the implant 2 and removes the tool, leaving the tape in place and partially looped around preferably the middle of the urethra 56. The second fixation area 16 adheres to the surrounding tissue it contacts and holds the second half of the implant 2 in place. During this procedure, the physician may check the color or other marking on the top and bottom sides 12, 14 of the implant 2 or the sheaths 46, 46', 46" to ensure that the tape is not twisted. If necessary, the physician may trim one or both fixation elements 16 to adjust the length of the implant.

The physician now uses forceps to separate and remove the plastic sheaths 46, 46', 46" that cover the top and bottom sides 12, 14 of the tape 4. The exposed tape is left implanted in the patient so that, over time, fibroblasts will proliferate and grow into the tape for securing the tape in the surrounding tissue. The fixation elements 16 fulfill their purpose for temporarily securing the implant. After absorption of the ETHISORB, the complete mesh length (including the parts in between the fixation elements) will have in-growth into surrounding tissue, leaving the implanted tape to provide support for the urethra 56.

Figure 12:
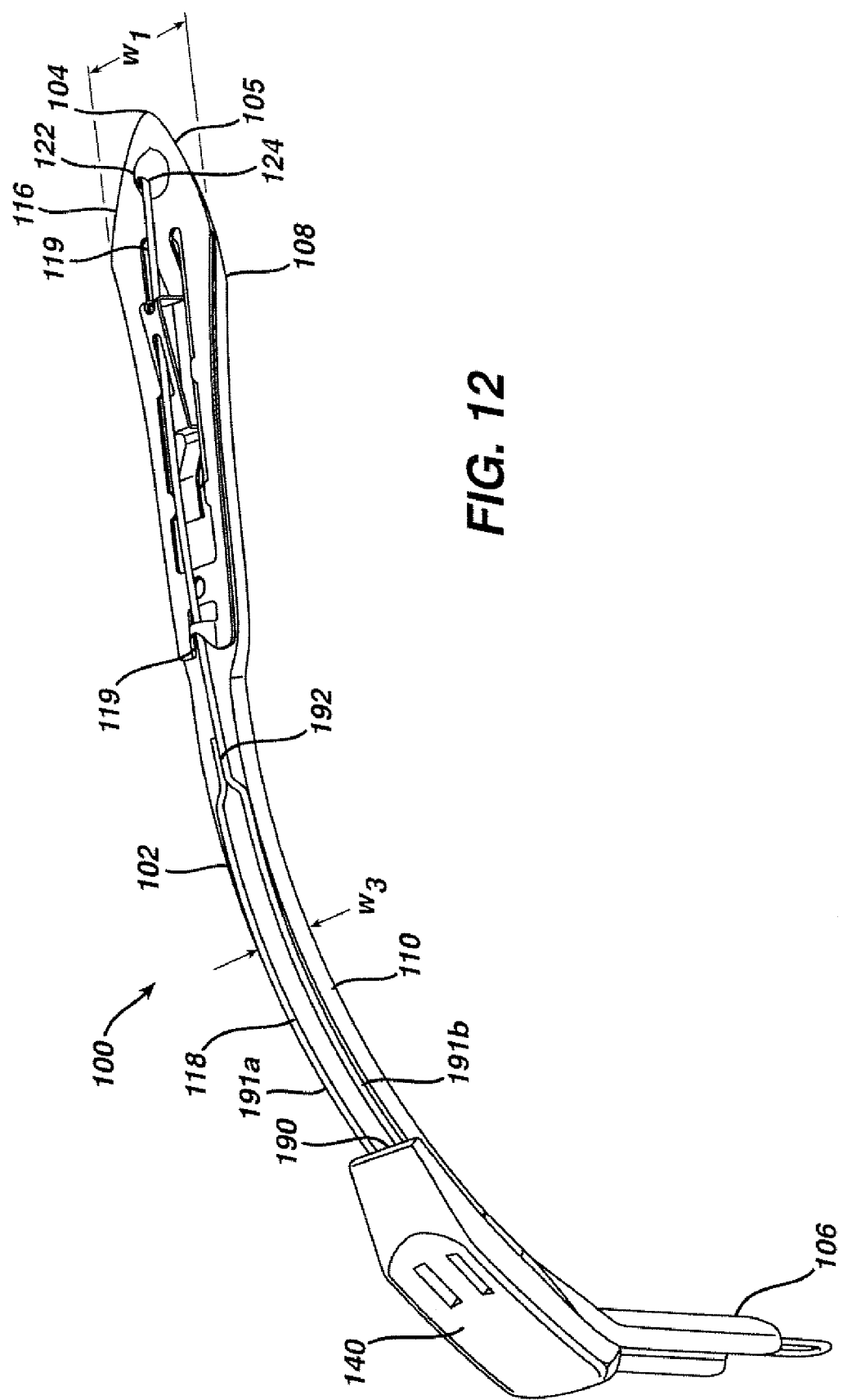
FIG. 12 is a perspective view illustrating another embodiment of an insertion device according to the present invention.

Referring once again to the embodiments of FIGS. 10, 10a and 14, another embodiment of an inserter particularly suited for use with the implants of the present disclosure is shown further in FIGS. 12-14. The inserter 100 preferably includes a first inserter device 102 having a contour or the like (see FIG. 13) that is particularly suited to substantially follow the desired insertion path as will be described further below. In the illustrated embodiment, the inserter includes a distal end region 103 including a tissue penetrating distal tip 104. The tissue penetrating distal tip preferably includes a cutting edge as opposed to a blunt edge. The first inserter device 102 includes a substantially planar portion 108, and a proximal end region 106 including a substantially curved portion 110. The substantially planar portion preferably has a length $l_1$ of approximately 1.2 inches, and a width of approximately 0.32 inches. Further, the curved portion 110 preferably has a length $l_2$ of approximately 1.5 inches over approximately 50 degrees. Preferably, the substantially planar portion is tangent to the curved portion 110, and a substantially straight proximal portion 113 of the first inserter device is position approximately 40 degrees to the tangent of the curved portion 110.

In the illustrated embodiment, the inserter also includes a stiffening element 116 that is coupled to and preferably has a substantially complementary periphery to the substantially planar portion of the first inserter device. The stiffening element provides additional stiffness to the inserter in the area to which the implant is secured as will be described in greater detail below. The stiffening element preferably is spaced slightly apart from the first inserter device, on the order of approximately 0.006 inches, by a plurality of small protrusions 130 or the like on either the inserter device or the stiffening element in order to enhance the efficiency and effectiveness of gas sterilization procedures by allowing sterilization gases to more freely flow between the parts. This stiffening element is a thin hardened material having an outer cutting edge 105, and a width $w_1$ that is slightly greater than that of the first inserter device 102, preferably on the order of 0.015 inches wider.

In the illustrated embodiment, the stiffening element also includes a first pass through element 132 that preferably is a spring type element. The first pass through element has a front portion 115 and a rear portion 117 (see FIGS. 13 and 14), both of which preferably extend upward substantially perpendicularly from the stiffening element. As will be described further below, when an implant is secured to the inserter, the first pass through element extends at least partially up through an aperture in the implant, so that the front portion 115 prevents rearward movement of the implant relative to the inserter and the real portion 117 prevent forward movement of the implant relative to the inserter. Further, when an implant is secure to the inserter, the spring type nature of the first pass through element biases it to return to a position that is more flush with the inserter. Thus, when the implant holding element 118 is retracted (as described below), the implant is more easily released. Finally, the rear portion 117 preferably has a length such that it fits within the thickness or profile of the inserter after the implant is released so that is does not snag or otherwise catch on tissue as the inserter is removed from the body following placement of the implant.

The inserter 100 further includes an implant holding element 118 that is movably coupled to the inserter device in an area towards the proximal end of the inserter device, such that it can be moved relative to the first inserter device as indicated by the arrow shown in FIG. 13. The purpose for this will become apparent from the further description below. For example, in the illustrated embodiment, the implant holding element 118 is comprised of single and double wire sections, which are held in place at multiple points. In the present embodiment, these multiple points include capture element 122, pass through elements 132, 114, and finger pad 140. Preferably, the finger pad 140 includes a projection 190 that extends between the two wires 191a, 191b, and acts as a stop against the portion a limit retraction of the implant holding element.

Figure 12A:
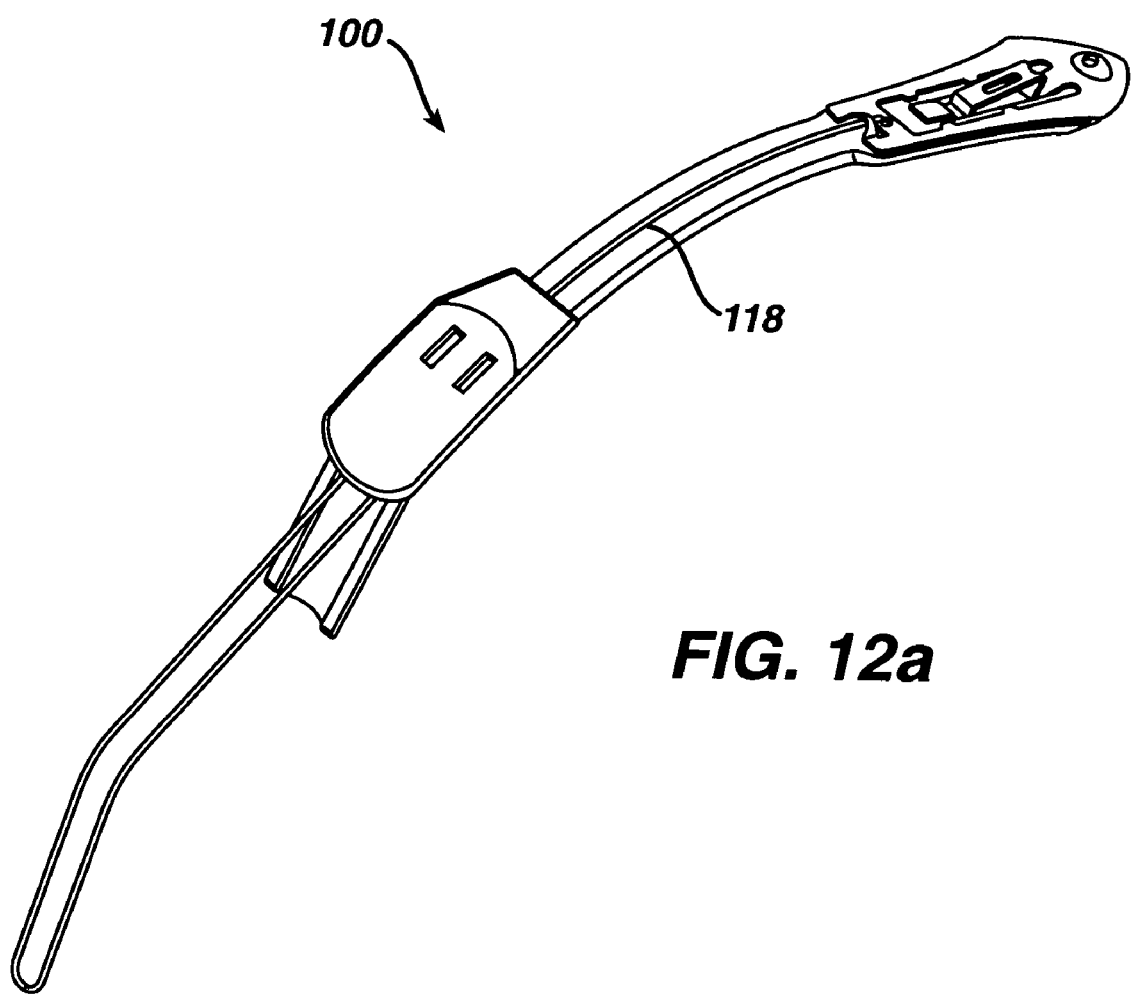
FIG. 12a illustrates the device of FIG. 12 with the implant holding element in a second position.

The distal end 120 of the implant holding element is removably coupled to the first inserter device, preferably by being received by a capture element 122 at the distal end of the inserter. By manipulation of the implant holding device by a user, however, the distal end of the implant holding element can be subsequently released from the capture element. In particular, movement of the implant holding device in the direction of the arrow shown in FIG. 13 will move the implant holding device to a second position shown in FIG. 12a wherein the implant holding element does not extend through the pass through element and is not received within the capture element. In this second position it also will not extend through the implant, thereby releasing the implant from the inserter device as will be readily understood by the further description below.

In the illustrated embodiment, the capture element 122 projects upwardly from a top surface of the stiffening element, and has an aperture 124 therein dimensioned to receive the distal end of the implant holding element. The capture element 122 also serves a second function in that it provides a buffer for the implant as it is inserted. Although this is a preferred embodiment, those skilled in the art will readily recognize that various forms and configurations for this capture element are possible so long as it serves the purpose of removably receiving the distal end of the implant holding element.

The inserter also preferably includes one or more pass through element (i.e., 132, 114) projecting upwardly from its top surface, and including one or more openings (i.e., 134, 119) therethrough. The openings may be of any configuration or shape so long as they allow the implant holding element to pass therethrough as shown best in FIG. 14. This feature at least partially maintains the position of the implant holding element relative to the inserter. Although the illustrated pass through elements are formed integral with the inserter, any pass through element suitable for at least partially maintaining the position of the capture element relative to the inserter could be used, such as suture loops or the like.

As indicated, the presently described inserter is particularly suited for use in conjunction with an implant similar in construction to that described in connection with FIG. 10, but having fixation elements 141 of the configuration shown in FIG. 14, which includes either substantially flat side edges 195a, 195b, or rough cut side edges as described above. In a preferred embodiment, the outermost width $w_2$ of the implant relative to the outermost width $w_1$ of the inserter has a ratio of approximately 1.4:1. This ratio is preferred to achieve a balance between insertion forces and user control as the implant is inserted into the connective tissue as described below. Lower and higher ratios offer different results depending on surgical needs and/or the type of tissue being penetrated. For example, lower ratios such as between 0.7 and 1.4 can increasingly reduce the insertion force and decrease the frictional forces of the implant on the surrounding tissue. These lower ratios, however, may offer less user control. Higher ratios, such as between 1.4 and 2.8 can increasingly raise the insertion force if used in tough tissue, but may not increase the insertion force in soft tissue.

Preferably, each of the fixation elements 140 are secured to the distal end region of the inserter device via the implant holding element 118 as shown. In the illustrated embodiment, the implant holding element 118 extends along and substantially adjacent to the top surface 119 of the first inserter device until it reaches the substantially planar region. At some point along the substantially planar region it begins to extend away from the first inserter device so as to leave a space therebetween as shown in FIG. 13. While spaced apart from the first inserter device, the implant holding device passes through the aperture 134 in the first pass through element 132, with its distal end 120 subsequently being received within the capture element 122. As shown in FIG. 14, to secure the implant to the inserter, the implant holding element extends upwardly through the implant before its distal end is received within the capture element 122. Preferably, the implant includes one or more apertures 135 extending therethrough to facilitate extension of the implant holding element through it, and to permit the pass through element 132 to extend upwardly through it as well.

According to one embodiment, the inserter 100 further includes a gripping element or finger pad 140 or the like positioned in the vicinity of the proximal end of the device. The gripping element is fixedly secured to the first inserter device 102 and has any configuration suitable to enhance gripping and manipulation of the device. In the illustrated embodiment, the gripping element is configured to receive a user's index finger. Additionally it has a tapered distal end to allow easy entry as the inserter 100 is pushed into the body. The finger pad 140 may also contains radio opaque material commonly used in medical devices to aid in determining if a lost or missing component has not been accidentally left in the patient. The inserter also may include one or two protective covers (not shown) over the cutting edge of the stiffening element to protect against damage or injury from the cutting edge prior to insertion.

The inserter provides several distinct advantages when inserting the implants described herein, as it allows the implant to be secured to the insertion device in a manner that minimizes the profile of the overall system. This is important in applications such as those described above because it is desirable to minimize tissue trauma other than that which is directly necessary to insert the implant. This is also important for visualization when placing the implant, as it is critical that the inserter minimize obstructing the surgeon's view during implantation. Another important aspect of the presently described inserter is that it provides a means by which to release the implant following proper placement without further manipulation of the implant. Further, the inserter 100 in combination with the described implant allows for forward and reverse adjustment of the implant before final release, and enables superior tactile feel by the surgeon before release. This is a significant advantage in that proper sling placement and tension can be achieved using the inserter device, and once this proper placement is achieved the implant is released without further movement. This is contrary to presently existing sling implants, where the mesh is initially implanted, then subsequently adjusted by pulling on the ends or center of the sling. Finally, the inserter device is designed so that it is not situated between the implant and the urethra (as compared to an insertion device that might "sandwich" the mesh between two opposing components) during placement of the implant, which has advantages with regard to proper positioning of the implant and visualization.

Figure 15A:
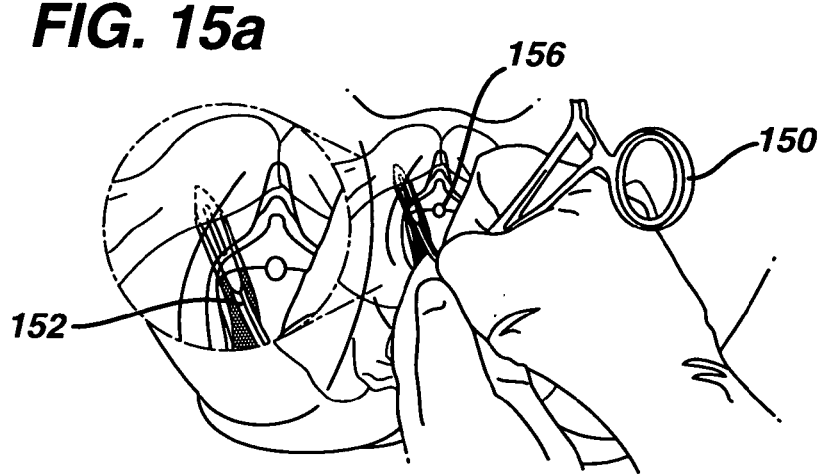
FIGS. 15a-c illustrates various insertion steps using an implant and insertion device according to the present invention.
Figure 15B:
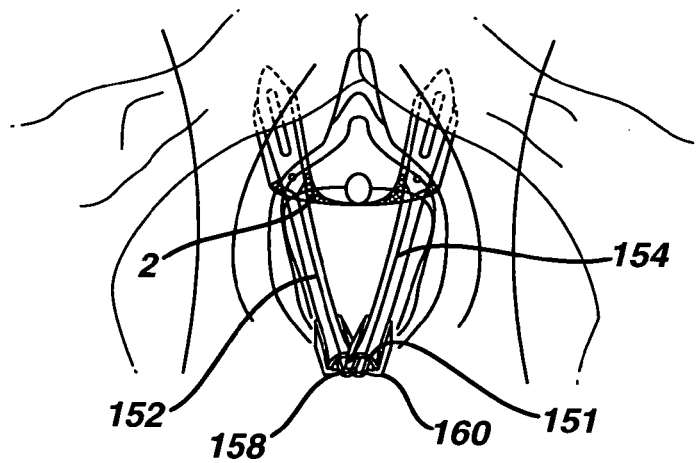

Another advantageous feature of the inserter of the present invention is that at least the cross-section of the curved portion 110 of the first inserter device has a substantially "v" shaped configuration 151, as can best be seen in FIG. 15b. This "v" shaped configuration enables the width $w_3$ of the curved portion to be reduced relative to the outermost width $w_1$ of the inserter, while still maintaining sufficient strength. It has been found that the reduced width relieves pressure against the urethra during placement of the implant. A larger width can place pressure against the urthra and cause a false positive, resulting in incorrect mesh placement after the inserters are removed. In a preferred embodiment the ratio of widths $w_1$ to $w_3$ is 2:1

Preferred methods for using the insertion device of FIG. 12-14 will now be described in detail with reference to FIGS. 15a-c and 16. An implant 2 having fixation elements 16 is preferably provided to a user with two inserters such as that described above, each secured to one end of the implant as shown in FIG. 15b. The patient is prepped for the procedure by draining the bladder, anesthetizing using local, regional or general anesthesia, and subsequently being placed in the lithotomy position. Using either forceps or an Allis clamp, the vaginal wall is grasped at each side of the urethra. A sagital incision about 1.5 cm long, starting approximately 1.0 cm from the external urethral meatus, is then made using a scalpel or the like. The incision will cover the mid-urethral zone and will allow for subsequent passage of the implant. Then, with a small pair of blunt scissors, two small paraurethral dissections of approximately 1.0 cm are made.

Figure 15C:
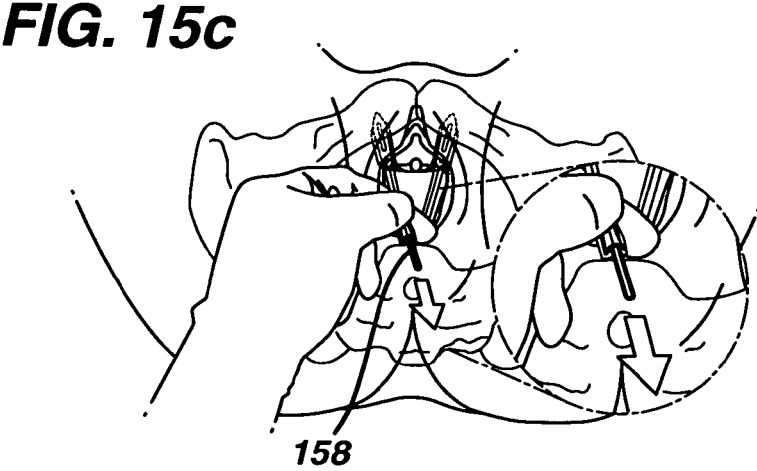

The proximal end 106 of one of the inserters is then grasped using any standard needle driver or holder 150 or the like, clamping over the holding element 118. For the "U" placement the distal end 108 of the inserter device is then oriented in approximately the 11 o'clock position towards the ipsilateral shoulder. With an index finger on the finger pad, the first 152 inserter and attached implant is inserted through the vaginal incision and first pre-dissected paraurethral dissection as shown in FIG. 15a, with the distal end of the insert device remaining in close contact with the inferior-posterior aspect of the pubic bone so that the implant is inserted into the connective tissue of the urogenital diaphragm. Insertion should stop when the insertion device is firmly in the connective tissue (approximately 4 cm from the distal end of the fixation element). The needle driver/holder is then uncoupled from the first inserter and coupled with the second inserter 154 in the same way. The process is then repeated on the other side of the urethra 156, leaving the insertion devices/implants as shown in FIG. 15b. The tape 4 should be placed tension free under the midurethra. Adjustments can be made as needed by further insertion or retraction with the first 152 or second 154 inserters. The implant is then released from both the first 152 and second 154 insertion devices by pulling on the respective implant holding elements 158, 160 as shown in FIG. 15c, rather than the mesh as is the case with other known devices. The insertion devices are removed and the incision closed, thereby completing the procedure.

Figure 16:
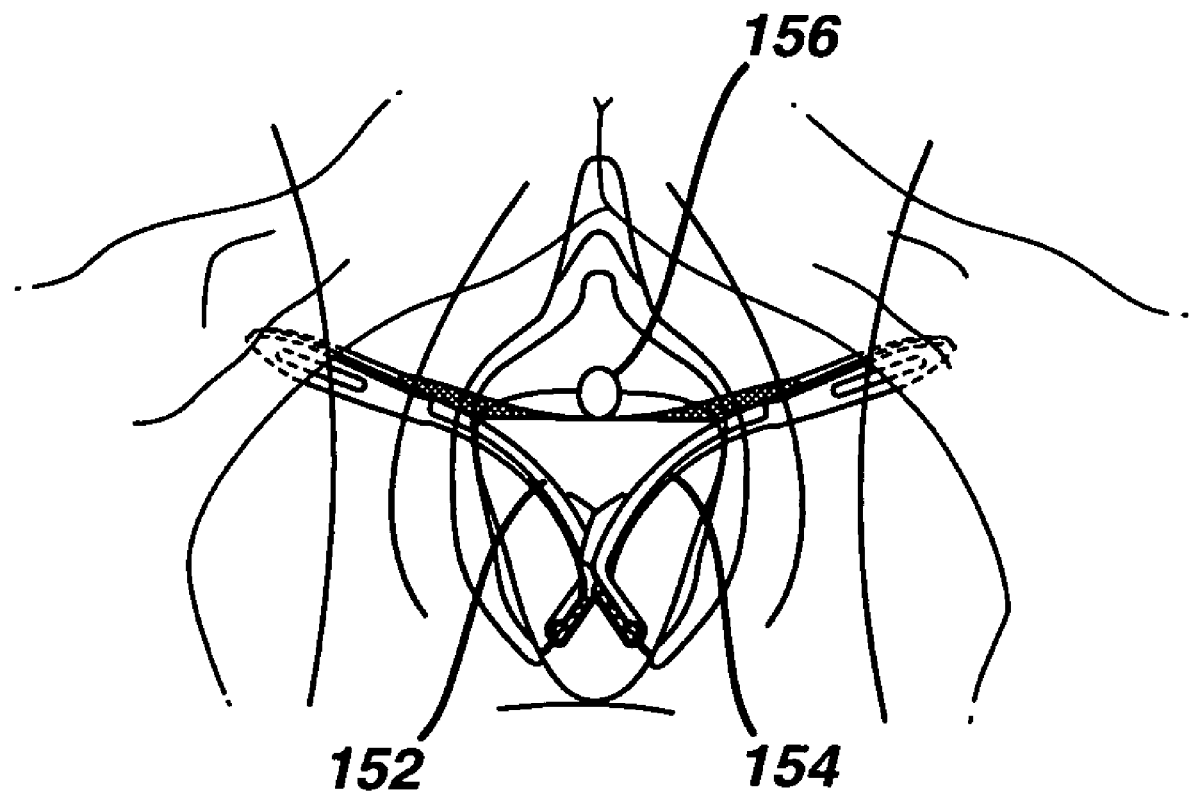
FIG. 16 illustrates an alternative placement of an implant according to the present invention.

According to another preferred method, the implant can be placed in a more lateral position as shown in FIG. 16, know to those skilled in the art as the "hammock" position. The procedure is substantially the same as that described above, except that the first inserter 152 is oriented in approximately the 9 o'clock position or parallel to the floor at an angle of approximately 45 degrees from the midline, towards the ischiopubic ramus. The distal end of the insertion device is inserted in close contact with the bone, but towards the obturator internus muscle, within which it is firmly secured. Adjustment is done with the inserter 100, not by pulling on the mesh.

The implants described herein may be advantageously implanted in a patient without the use of needles that pass through the whole body and without the need to form incisions in the abdominal wall, large pre-dissected tracts, or upper leg of the patient, and further without the need for bone anchors of the like. Not only is the procedure less emotionally traumatic to the patient than conventional procedures employing elongated curved needles, or hooked device that are used to snag and drag the mesh through the body, but also less invasive, as no incisions to the abdominal wall or upper leg of the patient are required. Because the actual implant of the present invention is smaller than conventional implants, this can potentially result in less surgical complications, less mesh rejections, and/or less mesh infections, and a shortened surgical procedure.

With the "U" implant placement of the present invention, the surgical implantation procedure may be performed on an outpatient basis under local, regional, or general anesthesia. Also, the procedure for implantation requires the use of a cystoscope, although the passage has less risk, as with all surgical procedures that pass near a structure there is always a risk of injury. The safety of the patient is further improved during the surgical implantation procedure, as there is less chance for complications due to the fact that there is no need to direct the "U" implant placement if done properly does not travel near the bladder or bowel or any large vessels as devices minimally invasive placement is intended to be at the lower edge of the pubic synthesis in the connective tissue near the pubic bone.

The "hammock" placement may similarly be performed on an outpatient basis under local, regional, or general anesthesia. The safety of the patient is even further improved over the "U" during the surgical implantation procedure, as there is no risk, if done correctly, to the bladder or bowel or any large vessels since the device path is not into the space of retzius. Additionally, the present invention offers yet further safety to currently known "hammock" type procedures that pass by or near the obturator bundle, which contains the nerve and artery. The implant of the present invention is preferably affixed into the internous muscle and it is not large enough to pass near the obturator bundle.

Figure 11:
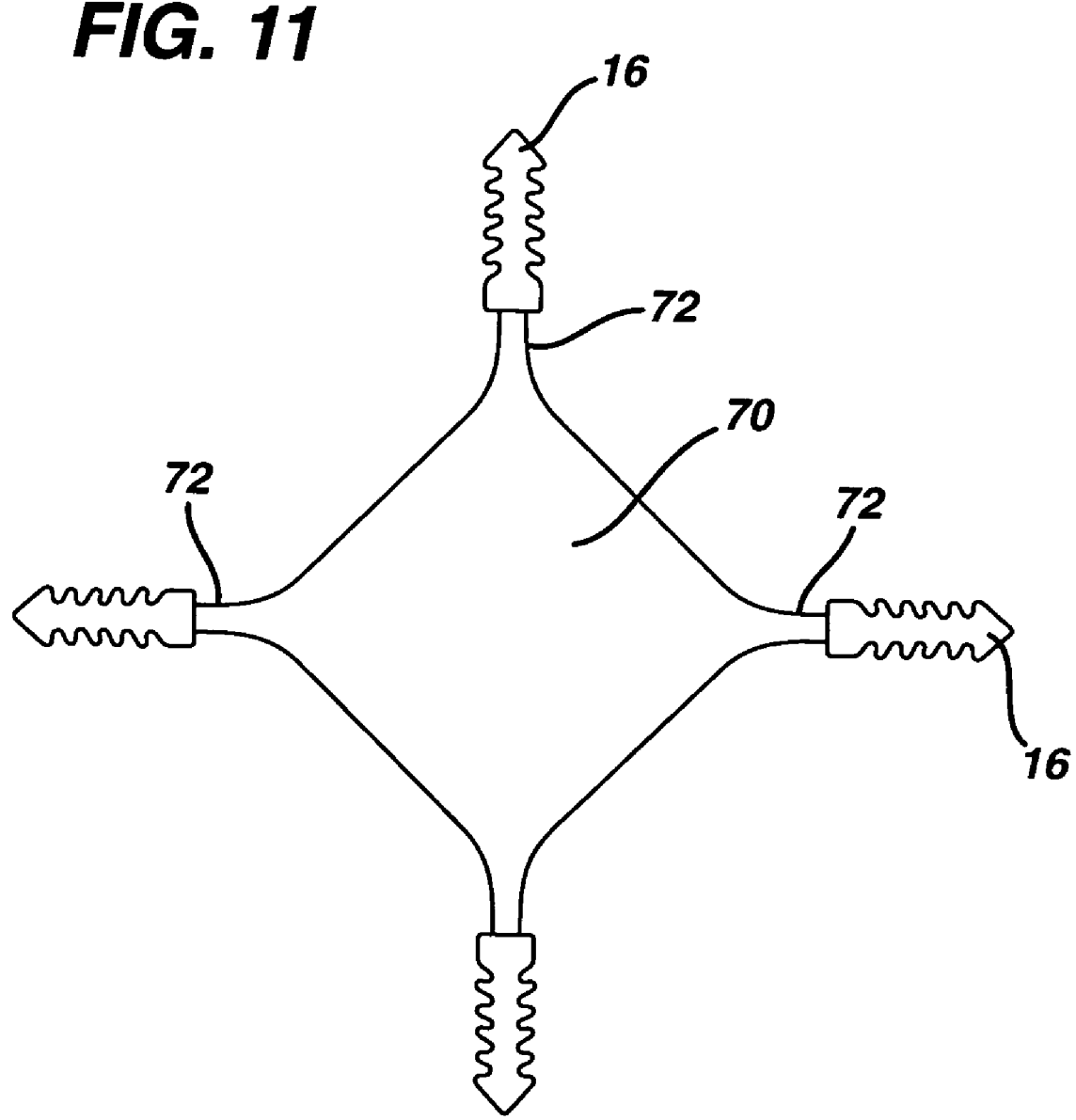
FIG. 11 illustrates another embodiment of an implant according to the present invention.

As indicated previously, although the present invention has been described in detail in relation to a sub-urethral tape, the invention is not so limited. The fixation elements described above can be incorporated to serve as fixation points for any type of mesh used in surgical procedures, such as pelvic floor repair or hernia repair, or plastic surgery, or restructuring of tissue. For example a mesh 70 such as shown in FIG. 11 (the shape is for illustrative purposes only, as any shaped mesh can be used) can incorporate one or more connection regions 72 to which fixation elements 16 can be secured. In the case of pelvic floor repair, for example, the mesh could be sized and shaped to treat a cystocele, with the mesh being secured in place using the fixation elements in a manner similar to that described above. For any and all plastic surgery used to change tissue position, for example, the device may look similar to the present invention and the insertion device shape, any width ratios of the inserter to implant, use of a covering, connection method and size may be altered to suit to th surgical application being attempted.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention, as is limited only by the appended claims.

What is claimed is:

1. A medical implant inserter comprising:

an inserter device having a distal end region including a tissue penetrating distal tip, a proximal end region, a capture element and a first pass through element both extending outwardly from the distal end region, the first pass through element being positioned at a location proximal of the capture element, an implant holding element having a proximal end and a distal end, the implant holding element being removably coupled at its distal end to the inserter device by being removably received within the capture element, and being movably coupled to the inserter device at a location proximal of the capture element, wherein a portion of the implant holding element lies substantially adjacent to the inserter device, and a distal end portion of the implant holding element extends to a position wherein it is spaced apart from the inserter device before being removably received within the capture element, and wherein the implant holding element passes through an opening in the first pass through element to thereby at least partially maintain the position of the implant holding element relative to the inserter device.

2. The inserter according to claim 1, wherein the distal end region of the inserter device further comprises a substantially planar portion and the proximal end region further comprises a curved portion.

3. The inserter according to claim 2, further comprising a stiffening element coupled to the substantially planar portion of the inserter device.

4. The inserter according to claim 3, wherein the stiffening element has substantially the same periphery as the substantially planar portion of the inserter device, and wherein the stiffening element has a stiffness greater than that of the inserter device.

5. The inserter according to claim 3, wherein the stiffening element is spaced apart from the substantially planar portion of the inserter device.

6. The inserter according to claim 1, wherein the implant holding element is a wire-like element.

7. The inserter according to claim 1, wherein the implant holding element is movable between a first position wherein the distal end is received within the capture element, and a second position wherein the distal end is not received within the capture element and is positioned proximal of and does not pass through the opening of the first pass through element.

8. The inserter according to claim 1, wherein the inserter device further comprises a second pass through element having at least one opening therethrough, wherein the implant holding element passes through said opening to thereby at least partially maintain the position of the implant holding element relative to the inserter device.

9. A medical device comprising:
an implant for implantation within a patient;
a first inserter for inserting the implant, the first inserter having a distal end region including a tissue penetrating distal tip, a proximal end region, a capture element located at the distal end region, and an implant holding element having a proximal end and a distal end, the distal end being removably received within the capture element, and the implant holding element further being movably coupled to the first inserter at a first location proximal of the capture element,
wherein the implant holding element extends from the first location at which it is movably coupled to the first inserter, and subsequently through the implant before being removably received within the capture element to thereby removably secure the implant to the insertion device.

10. The device according to claim 9, wherein the implant holding element extends through a first end region of the implant.

11. The device according to claim 9, wherein the implant further comprises a first fixation element at a first end and a second fixation element at a second end and a mesh therebetween having a stiffness less than that of the first and second fixation elements, and wherein the implant holding element extends through the first fixation element.

12. The device according to claim 11, wherein the first and second fixation elements have an outermost width and the distal end region of the first inserter has an outermost width, and wherein the ratio of the outermost width of the first and second fixation elements to the outermost width of the distal end region of the first inserter is approximately 1.4:1.

13. The device according to claim 11, further comprising a second inserter device having a distal end region including a tissue penetrating distal tip, a proximal end region, a capture element located at the distal end region, and an implant holding element having a proximal end and a distal end, the distal end being removably received within the capture element, and the implant holding element further being movably coupled to the second inserter device at a location proximal of the capture element,
wherein the implant holding element extends from a position substantially adjacent to the second inserter device, and subsequently through the second fixation element of the implant before being removably received within the capture element to thereby removably secure the second end of the implant to the second insertion device.

14. The device according to claim 9, wherein the insertion device further comprises a stiffening element substantially adjacent to the first fixation element.

15. The device according to claim 14, wherein the stiffening element is substantially adjacent to a substantially planar portion of the insertion device and has a substantially similar periphery as that of the substantially planar portion, and wherein the stiffening element has a stiffness greater than that of the inserter device.

16. The device according to claim 9, wherein the implant has an aperture therein through which the implant holding device passes.

17. The device according to claim 9, wherein the first insertion device further comprises a first pass through element extending outwardly from the distal end region at a location proximal of the capture element and having at least one opening therethrough, and wherein the implant further has an opening therethrough through which the first pass through element extends, and wherein the implant holding element extends through the implant and through the opening in the first pass through element before being removably received within the capture element.

18. The device according to claim 9, wherein the tissue penetrating distal tip includes a cutting edge.

19. The device according to claim 9, wherein the implant holding element is movable between a first position wherein the distal end is received within the capture element, and a second position wherein the distal end is not received within the capture element and is positioned proximal of and does not pass through the opening of the first pass through element so as to thereby release the implant from the insertion device.

20. A medical device comprising:
an implant for implantation within a patient having a first end, a second end, and top and bottom sides;
an inserter device for inserting the implant having a distal end region including a tissue penetrating distal tip, a proximal end region, a capture element positioned at the distal end region, and an implant holding element having a proximal end and a distal end that is removably received by the capture element when in a first position, wherein the implant holding element is movably coupled to the inserter device at a location proximal of the capture element, and wherein the implant holding element is movable to a second position wherein the second end is positioned proximal of and not received within the capture element,
wherein when the implant holding device is in the first position, at least a first end of the implant is positioned between the implant holding device and the inserter device to thereby secure the implant to the inserter device, and wherein when the implant holding device is in the second position, the implant is not positioned between the implant holding device and the inserter, and is not secured thereto.

21. The device according to claim 20, wherein the implant holding element is a wire-like element.

22. The device according to claim 20, wherein the distal end region of the inserter device further comprises a substantially planar portion and the proximal end region further comprises a curved portion.

23. The device according to claim 22, further comprising a stiffening element coupled to the substantially planar portion of the inserter device.

24. The device according to claim 23, wherein the stiffening element has substantially the same periphery as the substantially planar portion of the inserter device, and wherein the stiffening element has a stiffness greater than that of the inserter device.

25. The device according to claim 23, wherein the stiffening element is spaced apart from the substantially planar portion of the inserter device.

26. A method for implanting a suburethral implant comprising:

providing an implant including an implantable, elongated tape having a multiplicity of openings formed therethrough, the tape having a first end region and a second end region longitudinally opposite the first end region, and first and second bio-compatible fixation elements attached to the first and second end regions respectively;

providing first and second insertion devices each including a first inserter having a distal end region including a tissue penetrating distal tip, a proximal end region, a capture element located at the distal end region, and an implant holding element having a proximal end and a distal end, removably coupling the first and second fixation elements of the implant to the first and second inserters respectively by extending the respective implant holding element from a first location wherein it is movably coupled to the insertion device, through the fixation element and to a second location wherein its distal end is removably received within the capture element;

inserting the first inserter and attached first fixation element through a vaginal incision and into a patient's tissue on a first side of the urethra;

inserting the second inserter and attached second fixation element through the vaginal incision and into the patient's tissue on a second side of the urethra;

adjusting the first inserter and attached fixation element and the second inserter and attached fixation element to thereby properly position the implant to provide support to the patient's urethra;

uncoupling the first and second inserters from the first and second fixation elements substantially without further manipulation of the implant; and leaving the implant implanted within the body without further adjustment thereof.

\* \* \* \* \*